(12) United States Patent  
Hu et al.

(10) Patent No.: US 7,397,232 B2
(45) Date of Patent: Jul. 8, 2008

(54) COULTER COUNTER HAVING A PLURALITY OF CHANNELS

(75) Inventors: Jun Hu, Fairlawn, OH (US); Jiang Zhe, Copley, OH (US)

(73) Assignee: The University of Akron, Akron, OH (US)

( * ) Notice: Subject to any disclaimer, the term of this patent is extended or adjusted under 35 U.S.C. 154(b) by 0 days.

(21) Appl. No.: 11/584,945

(22) Filed: Oct. 23, 2006

(65) Prior Publication Data

US 2007/0159156 A1    Jul. 12, 2007

Related U.S. Application Data

(60) Provisional application No. 60/729,262, filed on Oct. 21, 2005.

(51) Int. Cl.
*G01N 27/00* (2006.01)
*G01N 15/00* (2006.01)

(52) U.S. Cl. ............... 324/71.4; 324/71.1; 73/865.5

(58) Field of Classification Search .............. 324/71.1, 324/71.3, 71.4, 691–693, 713, 439, 450; 73/61.71, 61.73, 865.5, 861.41; 702/26, 702/29

See application file for complete search history.

(56) References Cited

U.S. PATENT DOCUMENTS

| | | | | |
|---|---|---|---|---|
| 2,656,508 A | | 10/1953 | Coulter | |
| 3,793,587 A | * | 2/1974 | Thom et al. | 324/71.1 |
| 4,157,498 A | * | 6/1979 | Johnson | 324/71.1 |
| 4,237,416 A | * | 12/1980 | Zold | 324/71.1 |
| 4,760,328 A | * | 7/1988 | Groves | 324/71.4 |
| 5,376,878 A | * | 12/1994 | Fisher | 324/71.4 |
| 6,175,227 B1 | * | 1/2001 | Graham et al. | 324/71.4 |
| 6,300,626 B1 | * | 10/2001 | Brock et al. | 250/287 |
| 6,426,615 B1 | * | 7/2002 | Mehta | 324/71.4 |
| 6,703,819 B2 | * | 3/2004 | Gascoyne et al. | 324/71.4 |
| 6,959,618 B1 | * | 11/2005 | Larsen | 73/865.5 |
| 7,060,992 B1 | * | 6/2006 | Barney | 250/458.1 |

* cited by examiner

*Primary Examiner*—Andrew H Hirshfeld
*Assistant Examiner*—Hoai-An D Nguyen
(74) *Attorney, Agent, or Firm*—Roetzel & Andress; George W. Moxon, II

(57) ABSTRACT

The present invention generally relates to a method for rapidly counting micron and/or submicron particles by passing such particles through any of a plurality of orifices simultaneously with an ion current and measuring the signal generated thereby. The present invention also generally relates to a device for practicing the method of the present invention. Some embodiments can include methods and/or devices for distinguishing between and counting particles in mixtures. Still other embodiments can include methods and/or devices for identifying and/or counting bioparticles and/or bioactive particles such as pollen.

20 Claims, 33 Drawing Sheets

⊕ Positive ion
○ Negative ion

⊕ Positive ion
○ Negative ion

COULTER COUNTER HAVING A PLURALITY OF CHANNELS

RELATED APPLICATION DATA

This application claims priority to U.S. Provisional Patent Application No. 60/729,262 filed Oct. 21, 2005 now pending, which is incorporated herein by reference in its entirety.

Development of this invention is funded United States Government grant Nos. NSF DMR 0210508 and NIH R15 DK61316-01. The U.S. Government may have certain rights in this invention.

BACKGROUND OF THE INVENTION

The present invention is generally related to a multichannel particle counting method and a device for practicing the method. Such counters can be used to count micro-scale and/or nano-scale particles and the like. Counters within the scope of the present invention generally operate by sensing changes in resistance, conductivity, conductance or the like. More particularly, as a particle passes through a channel, it disrupts the ion current therein, thus increasing the channel's resistance.

Quantitative measurements of the size and concentration of micro and nano scale particles has been accomplished using Coulter counters. A typical Coulter counter device comprising a single micropore that separates two chambers containing electrolyte solutions. When a particle flows through the microchannel, it results in the electrical resistance change of the liquid filled microchannel. The resistance change can be recorded in terms of current or voltage pulses, which can be correlated to size, mobility, surface charge and concentration of the particles. Due to the simple construction of these devices and the reliable sensing method, Coulter devices have found application in a broad range of particle analyses from blood cells to polymeric beads, DNA, virus particles and even metal ions.

One substantial disadvantage of existing Coulter counters is their low throughput efficiency, which substantially extends measurement times. Coulter counting measurement relies on particles passing through a tiny orifice (microchannel) one by one from one chamber to the other. Thus, in order to complete sampling of a small number of particle solutions, thousands of micro or nanoparticles have to pass through the orifice one by one, which could be prohibitively time consuming. For instance, one estimate shows that a sample having a particle concentration of $10^8$ particles/mL (v/v ratio 0.026%) requires 27.7 hours to complete a measurement, assuming each particle takes about 0.05 seconds to pass through the orifice, only one particle is resident in the orifice at any given time, and assuming a 0.01 mL sample volume. The measurement time is further extended as the orifice size decreases.

A variety of approaches to alleviating the time-measurement issue have been tried in the art. For instance, electroosmosis and electrophoresis have been applied to drive particles and electrolyte fluids. However, both methods have fallen short. Particularly, in order to obtain a sufficient fluid velocity, a strong external electric field must be applied leading to high power consumption, which is not practical for most biological applications. Furthermore, electroosmosis and electrophoresis only drive charged particles. Thus, if the particles are only slightly charged or neutral, electric forces are too weak to substantially shorten measurement time. Accordingly, there is a deficiency in the art in that it lacks a high throughput particle counting method and device, which is compatible with biological particles.

The present invention overcomes the challenges and deficiencies of the prior art by providing a particle counting method and device having a plurality of orifices, which are capable of counting particles in parallel with one another. Furthermore, such systems are compatible with biological particles inasmuch as it circumvents the need for electrophoretic or electroosmotic fields. Thus, the present invention fills a substantial gap in the art.

SUMMARY OF THE INVENTION

The present invention is generally directed to a multichannel particle counting device comprising a membrane dividing a first reservoir and a second reservoir; the membrane including a plurality of orifices disposed therethrough, through which the first and second reservoirs maintain fluid communication; the orifices further including a control electrode, wherein each control electrode is substantially electrically isolated from every other control electrode; the first reservoir including a first electrode, which electrode is in electrical communication with a power supply; the second reservoir including a second electrode, which electrode is in electrical communication with a measuring circuit; and the reservoirs containing an electrolyte solution.

A method for rapidly counting particles comprising the steps of charging one reservoir of the foregoing device with at least one particle to be measured; applying a voltage across the first and second electrodes; allowing the particles to migrate from one reservoir to the other through the plurality of orifices; detecting the signals generated by particles passing through the plurality of orifices; deconvoluting the signals detected; counting the deconvoluted signals; and correlating the signals to a number of particles.

DETAILED DESCRIPTION OF THE INVENTION

The present invention generally relates to a method for rapidly counting particles using a plurality of orifices for simultaneously sensing particles. The present invention also generally relates to a device for practicing the method of the present invention.

The method of the present invention includes providing a plurality of orifices that are capable of passing particles to be counted, wherein the diameter of the orifices is such that they can pass the particles one at a time, i.e., in single file. In general the orifices separate two electrolyte solutions, wherein one solution is in electrical communication with a cathode and the other is in electrical communication with an anode. When a voltage is applied across the cathode/anode pair, an ion current flows through the orifices. Thus, a signal is generated when at least one particle enters at least one orifice, thereby obstructing the flow of ion current and raising resistance. The signal can be read conveniently in terms of current or voltage. Furthermore, the present invention simultaneously detects particles in a plurality of orifices. Since these orifices are in a parallel electrical relationship, the signals generated thereby are multiplexed, and thus must be deconvoluted. The Hardmard transformation makes it possible to deconvolute the signal of the multiplexed particle counting device of the present invention.

Membranes within the scope of the present invention can be fabricated from a wide variety of materials including without limitation organic polymers such as polymethyl methacrylates, polycarbonates, polyimides, polyphenols, chlorinated polyolefins, and the like. Additionally, membranes within the scope of the present invention can be fabricated from silicon, n-type silicon, p-type silicon, and the like. Membrane materials within the scope of the present invention should be stable under ordinary usage conditions, and should be capable of forming the pores and other micro and/or nano structures comprising the present invention.

Electrodes within the scope of the present invention can be fabricated from any of a variety of materials including without limitation, Ag|AgCl, platinum, and graphite electrodes.

Any of a variety of electrolytes can be used as the electrolyte of the present invention. In general, acceptable electrolytes are compatible with the selected electrode(s), and comprise cations and anions having similar mobilities. For instance, when the selected electrode is Ag|AgCl acceptable electrolytes include, without limitation, KCl and NaCl.

Figure 1:
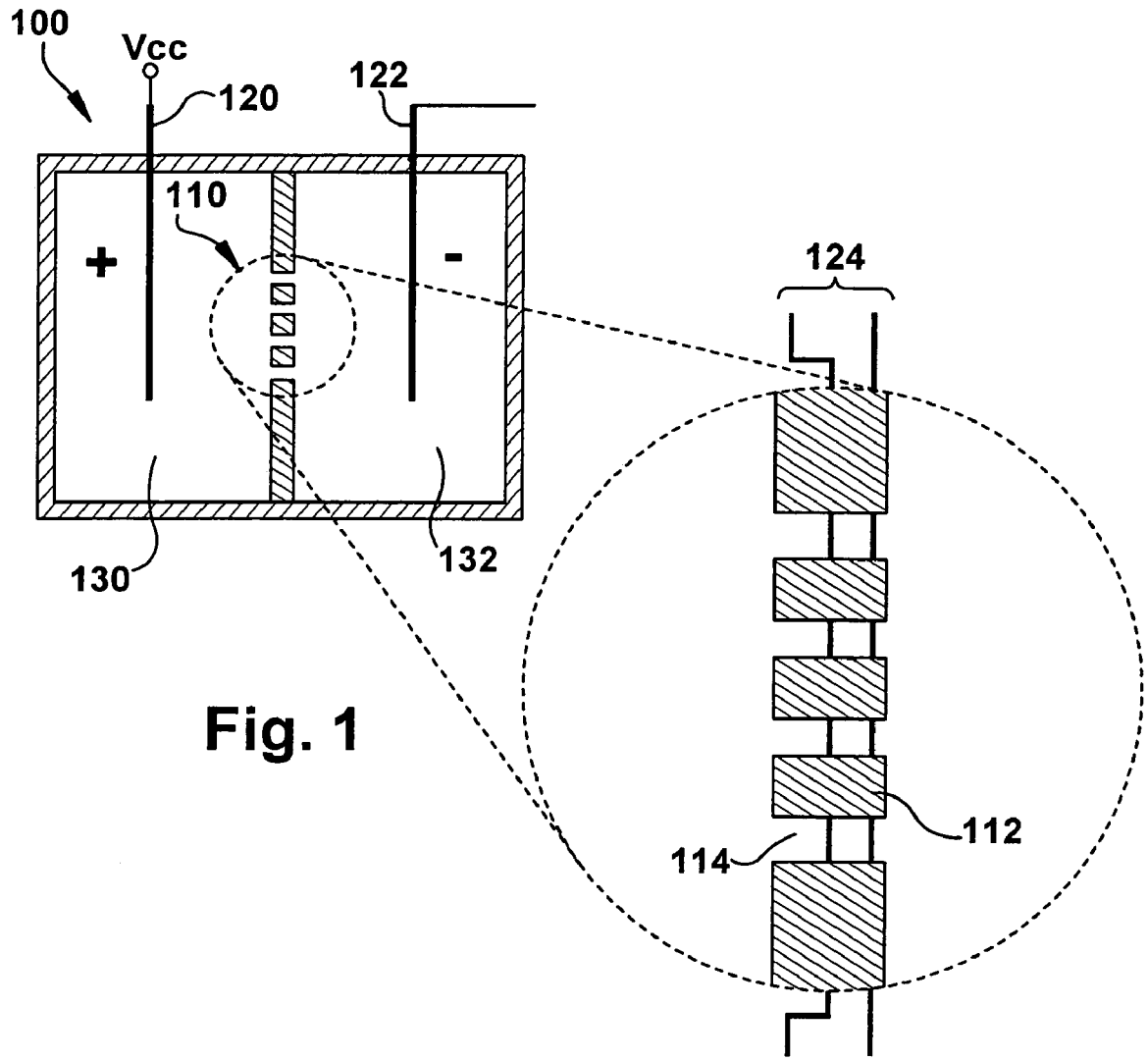
FIG. 1 is a schematic showing the a multichannel particle counting device.

An example of the present invention is shown in FIG. 1. Four microchannels 110 are formed using insulating blocks 112 (i.e., isolation blocks). Each individual microchannel 114 (i.e., orifice) includes a control electrode 124, which carries out control and measurement functions the nature of which will become apparent in the following paragraphs. Furthermore, each control electrode 124 is insulated from every other control electrode 124 so that sensing events occurring in one microchannel 114 do not affect sensing events in other microchannels 114. The plurality of microchannels 110 separate two electrolyte solutions contained in separate reservoirs 130, 132. One reservoir 130 is in electrical contact with a cathode 120 and the other is in electrical contact with an anode 122. When a suitable voltage (e.g., 2.7 V) is applied across the electrodes an ion current is generated, which runs through the plurality of microchannels 110. In this embodiment, either the cathode 120 or anode 122 is in electrical communication with a power supply, while the other electrode is in electrical communication with a measurement circuit. Signals are generated when one or more particles enter one or more microchannels 114 thereby raising the resistance to ion current therein and causing a consequent increase in voltage. Each microchannel causes its own voltage and/or current signal, which superpositions with the signals of each other microchannel.

Figure 2:
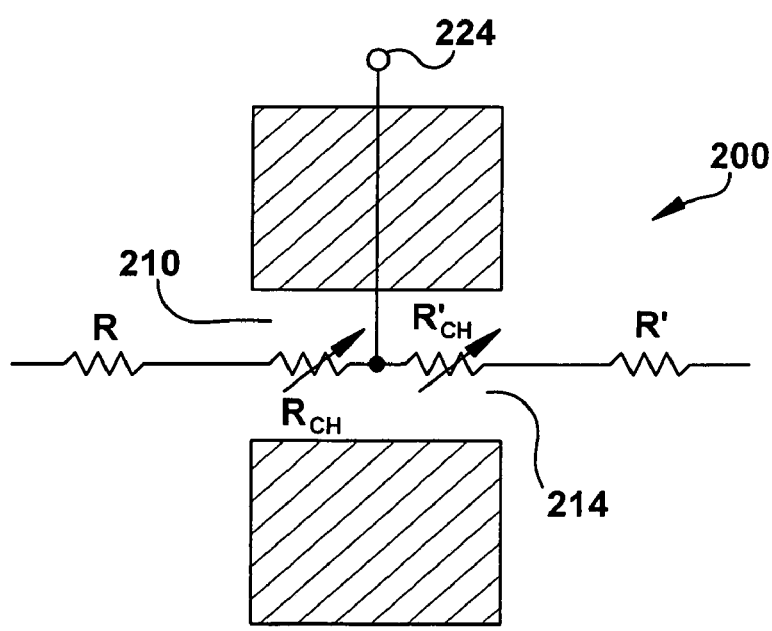
FIG. 2 is a diagram pictorially showing the resistance of each sensing element. Note that R and R' (i.e., the resistances of the electrolytes outside the channel) can be neglected when compared to the channel resistances $R_{ch}$ and $R'_{ch}$.

FIG. 2 shows the equivalent resistance model of an individual channel. The resistances R and R' are that of the fluids in the reservoirs between the cathode (or anode) and the channel. $R_{ch}$ is the channel resistance and its value is a function of channel diameter, length and ion solution in the channel. When a particle enters the channel 214 it displaces some ions and from the channel 214, which results in an increase in the channel resistance. The control electrode 224 is positioned in the middle so that the channel resistance is split into two resistances $R_{ch}$, $R'_{ch}$. Thus, the control electrode 224 forms a node with the two resistances.

Figure 3:
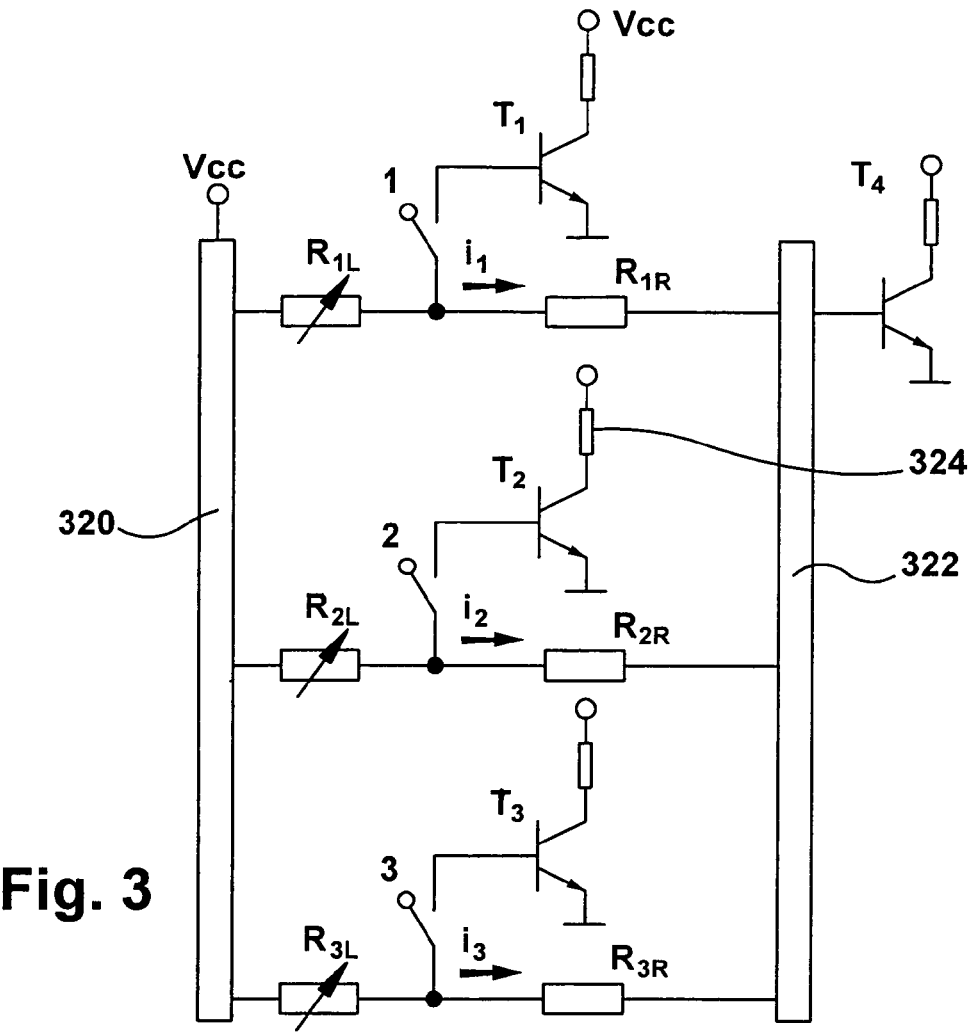
FIG. 3 is an electrical schematic showing an example embodiment of the present invention comprising a 3-channel multiplexing particle counting device.

In order to detect a particle passing through a particular channel the response of each individual channel needs to be obtained in the form of a current or voltage pulse. However, since all of the channels are in electrical communication with the electrolyte solutions the signal sensed by the measurement circuit is the sum of the signals from all channels at any given time. The present invention is able to deconvolute the raw superposition of signals, and records the signals of each individual channel. FIG. 3 is a schematic of a measurement circuit for a 3-channel device. $V_{cc}$ is kept at a high voltage level, such as from about 1 V to about 4 V (e.g., 2.7 V). Each control electrode 324 is connected to a transistor (T1, T2, or T3). The measurement circuit has a transistor (T4) in common emitter configuration. T4 is always kept on, so that the voltage at node 4 is kept at approximately 0.7 V. If T1 is on, the voltage at node 1 is 0.7 V, so that there is no current input to transistor 4 from channel 1. Because of the measurement configuration, the output of the transistor T1 is representative of the resistance of channel 1 ($R_{1L}$). Similarly, if T2 and T3 are open, we could measure the output of T2 and T3, which are representative of the resistances of channel 2 and 3 ($R_{2L}$, $R_{3L}$) respectively. On the other hand, if T1 is off then current $i_1$, which is representative of resistance ($R_{1L}$), will be one input to T4 or the sum of any channels selected. Similarly, if T2 and T3 are off then currents $i_2$ and $i_3$ will be the input to transistor T4. Therefore, by controlling the on/off state of control electrodes it is possible to turn the current on and off from each channel and measure the sum of the responses of any selected channels.

The raw signal obtained from the measurement circuit is deconvoluted according to the following process. The on/off states of the four control electrodes (S1, S2, S3) are controlled with a pseudorandom sequence. The current i4, measured from transistor 4, is the sum of the current through selected channels. A channel is selected when its transistor is off. Thus, if a control electrode is off the current through the channel will be input Transistor 4.

TABLE 1

| S1 | S2 | S3 | i4 |
|---|---|---|---|
| OFF | OFF | OFF | i1 + i2 + i3 |
| OFF | OFF | ON | i1 + i2 |
| ON | OFF | OFF | i2 + i3 |

Desired current combinations can be measured (Matrix Y) by setting the desired switching sequence (matrix S) of control electrodes. For the sequence code in Table 1, the sequence matrix S can be written as:

$$S = \begin{pmatrix} 1 & 1 & 1 \\ 1 & 1 & 0 \\ 0 & 1 & 1 \end{pmatrix}$$

The Hardmard transformation can be used to find the current response of individual channels since the switching sequence is known. Therefore the current response of individual channel X, can be calculated as the dot product of matrix Y and the inverse of matrix S:

$$X = S^{-1} \cdot Y$$

Furthermore, four combinations are needed in order to solve this equation because it entails four unknown currents.

In a Hardmard Transformation, the mean square error is reduced by a factor of $(n+1)^2/4n$ indicating that the signal-to-noise ratio is increased by a factor of $(n+1)/4n^{1/2}$. Thus, as the number of channels increases, the signal-to-noise channel improves.

One embodiment of the present invention comprises a device 400 for quantitatively detecting the concentration and particle size of pollen in air. For instance, the multiplexed particle counting device 400 of the present invention can be outfitted with an air sampling device 410 according to FIG. 4. As shown, a sampling bottle 412 has an air sampling port 414, which is vented to the atmosphere. Furthermore, it is fitted with an electrolyte intake port 420, and fed therethrough by an electrolyte reservoir 422. Additionally, the sample bottle has two output ports 430, 440. One is a vapor line 440, which is in fluid communication with a vacuum pump 442, so that when the vacuum pump 442 operates gas is drawn from the sample bottle 412. The other output port is a liquid output 430, which carries electrolyte solution to the particle counting portion 432 of the device 400. Optionally, the airborne pollen sampling device can additionally include a component 434 for adding antibodies to the electrolyte solution before it reaches the particle counting portion 432 of the device 400.

Figure 4:
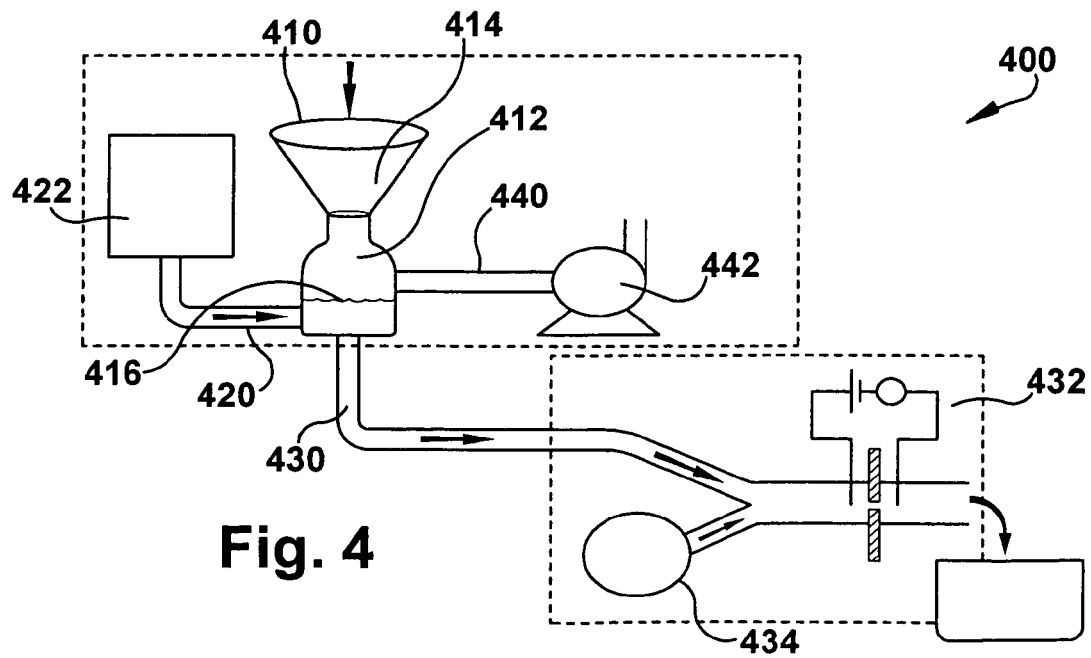
FIG. 4 is a diagram of a airborne pollen sampling device fitted with the multichannel particle counting device of the present invention.

This system 400 operates as follows. The vacuum pump 432 draws air into the sample bottle 412 through air intake port 414. Any particles that may be present impact the liquid electrolyte surface 416 and are deposited therein while the gas is drawn out of the sample bottle 412 through the vacuum pump 442. The particle-laden electrolyte solution then travels through the electrolyte output port 430 and down the liquid line leading to the particle counting portion 432 of the device 400, where the particles are then counted. Furthermore, the liquid can be induced to flow through the counting portion 432 by maintaining a positive pressure on the sampling side of the counting portion 432. For instance, as shown in FIG. 4, an electrolyte reservoir 422 is included, which can be elevated so that a gravity-induced pressure gradient is created, which drives liquid flow.

Another embodiment of the present invention comprises a device for detecting the concentration and particle size of chemical and/or biological warfare agents such as weaponized (i.e., aerosolized) anthrax. In still another embodiment, the present invention comprises a device for detecting toxins, impurities, or microbial or viral contaminants in waters, such as drinking water. Still another embodiment of the present invention comprises a device for rapidly counting blood cells, and/or comparing the number of red blood cells to white blood cells.

Figure 5:
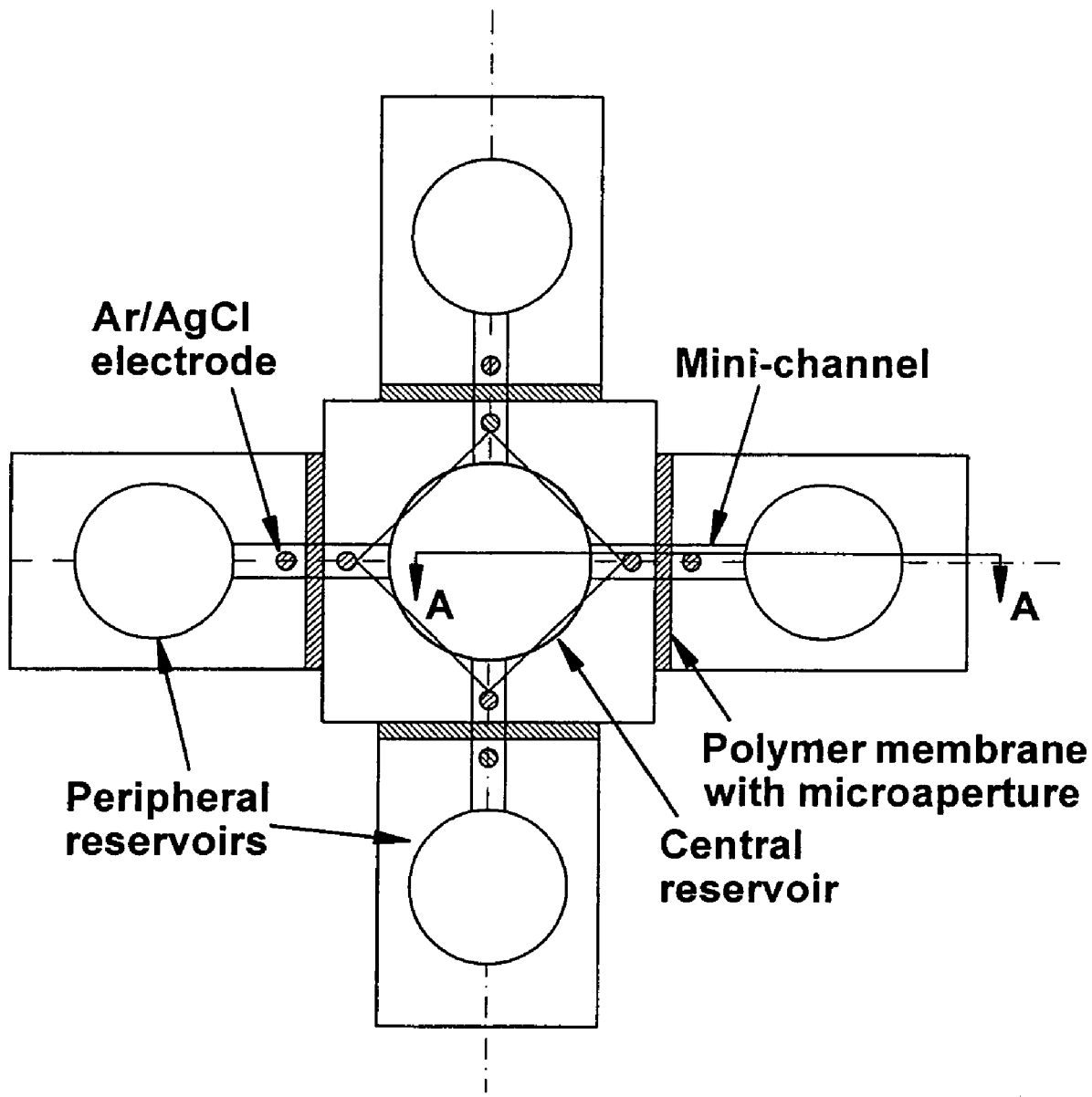
FIG. 5 is a drawing of a multi-aperture embodiment for microparticle detection.

I. Pollen Detection Embodiments:

One non-limiting embodiment of the present invention comprises a multi-aperture Coulter counter, as shown in FIG. 5. This embodiment comprises four peripheral reservoirs and a central reservoir. Each peripheral reservoir is connected to the central reservoir through a miniature channel. According to this embodiment, a micro-scale aperture in the middle of each mini-channel is used for sensing.

In this embodiment, the central reservoir and one half of each of the four mini-channels can be formed by drilling holes in a polymethyl methacrylate (PM) block. Furthermore, each of four additional PM blocks can be drilled to form the other half of a mini-channel and a peripheral reservoir. After the holes are drilled, the PM blocks can be cleaned, for example, with ethyl alcohol and/or sonicated in an ultrasound bath. The microapertures are fabricated by piercing four polymer membranes with a heated micro needle. The membranes can be examined under a high-precision microscope, and the microapertures are found to have diameters between 90 μm and 110 μm, as shown in Table 2.

TABLE 2

|  | Aperture 1 | Aperture 2 | Aperture 3 | Aperture 4 |
| --- | --- | --- | --- | --- |
| Diameter D | 110 μm | 110 μm | 90 μm | 100 μm |

The nominal thickness of the membrane is about 100 μm. However, due to the hot-piercing microaperture fabrication process, the length of each microaperture might change considerably from the nominal thickness of the membrane, which is determined later.

According to this non-limiting embodiment, the first channel can be formed by applying epoxy to one mini-channel side of the PM block with the central reservoir, and to the mini-channel side of one of the PM blocks with a peripheral reservoir. A membrane can be placed between the two blocks, carefully aligned so that its microaperture is centered between the two halves of the mini-channel. The blocks are then clamped together for two to five hours, or until the two blocks and the membrane are firmly attached. A pair of 1 mm holes, located 5 mm away from the membrane on both sides, can be drilled in the PM blocks. The Ag/AgCl electrodes are placed on both sides of the membrane through the 1 mm holes. Then epoxy can be applied to fix the electrodes and seal the mini-channel. The same procedure is repeated for the other three peripheral blocks to form a four-aperture sensor. One of ordinary skill in the art will readily appreciate that a variety of alternative materials, fabrication techniques, and electrodes can be used to form a device within the scope of the present invention.

Figure 6A:
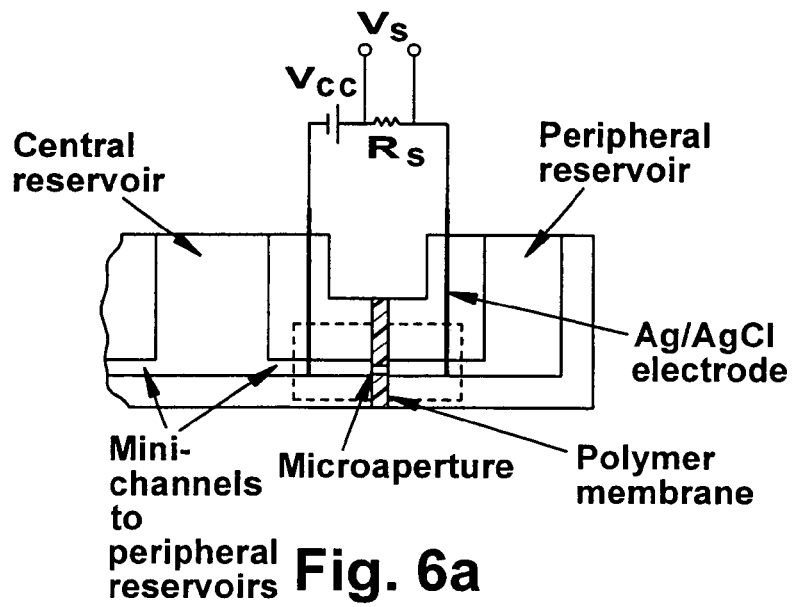
FIG. 6 (a) is a schematic front view of a single channel of a multi-aperture embodiment, (b) is a magnified view of a single channel; and (c) is a drawing of an circuit equivalent of a single channel.
Figure 6B:
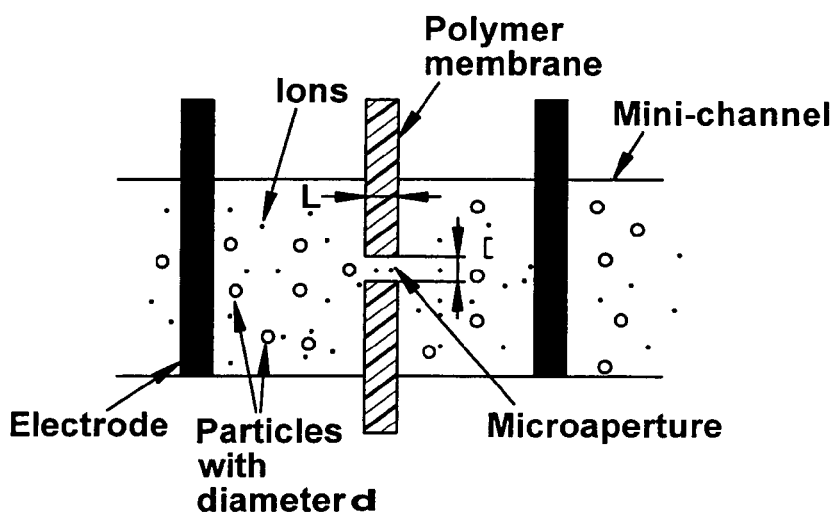
Figure 6C:
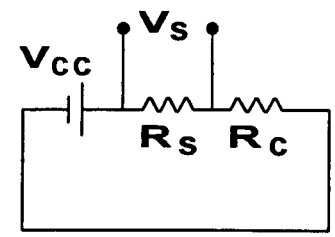

FIG. 6(a) shows the sectioned front view of a single sensing channel (across the A-A line in FIG. 5), along with the measurement setup. $R_s$ is a known external sampling resistor. The Ag/AgCl electrodes placed on both sides of the membrane are used to apply a constant DC voltage VCC across the channel. FIG. 6(b) shows a magnified drawing of the mini-channel, microaperture and electrodes. The measurement architecture of one sensing channel is electrically equivalent to the circuit in FIG. 6(c), where $R_c$ is the resistance of the electrolyte-filled microaperture.

As a particle passes through the microaperture there is a change in the electrical resistance of the aperture. This leads to a change in the voltage $V_s$ across the measurement resistance $R_s$. From the circuit model in FIG. 6(c), the relative change in the resistance of the microaperture is given by:

$$\delta R_c / R_c = \frac{(V_s - V_s')V_{cc}}{(V_{cc} - V_s)V_s'} \quad (1)$$

where $\delta R_c$ is the change in aperture resistance, $R_c$ is the resistance of the aperture when no particles are present, $V_{cc}$ is the applied DC voltage, $V_s$ is the voltage measured across the sampling resistor when the aperture is filled only with electrolyte solution and $V_s'$ is the peak voltage measured across the sampling resistor as a particle passes through the microaperture.

For a microaperture with length L and diameter D (see FIG. 6(b)), the change in resistance as a particle passes through it is given by:

$$\delta R_c / R_c = \frac{d^3}{L'D^2}\left[\frac{D^2}{2L^2} + \frac{1}{\sqrt{1+\left(\frac{D}{L}\right)^2}}\right] \quad (2)$$

where d is the diameter of the particle, L' is the corrected aperture length to account for fabrication artifacts, which equals L+0.8D. Equation 2 holds when $(d/D)^3 < 0.1$, as is the case in this and other embodiments. Thus, the particle diameter can be calculated from the relative change in resistance according to:

$$d = \sqrt[3]{\frac{\frac{\delta R_c}{R_c} L'D^2}{\frac{D^2}{2L^2} + \frac{1}{\sqrt{1+\left(\frac{D}{L}\right)^2}}}} \quad (3)$$

Figure 7:
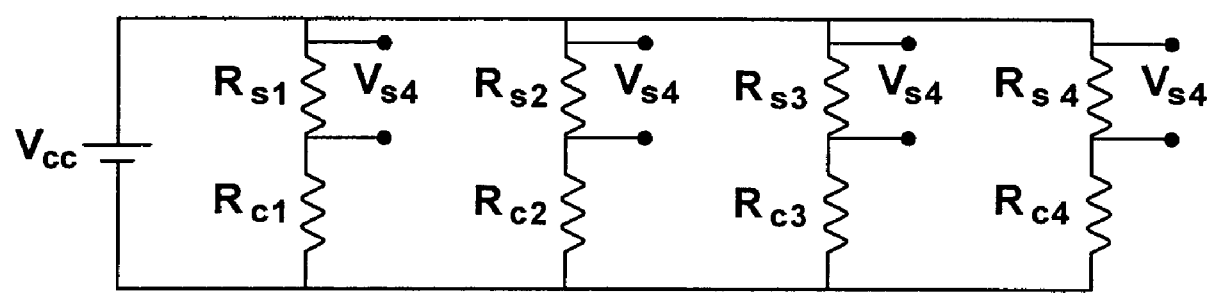
FIG. 7 is a equivalent electric circuit of a four-aperture embodiment.
Figure 8A:
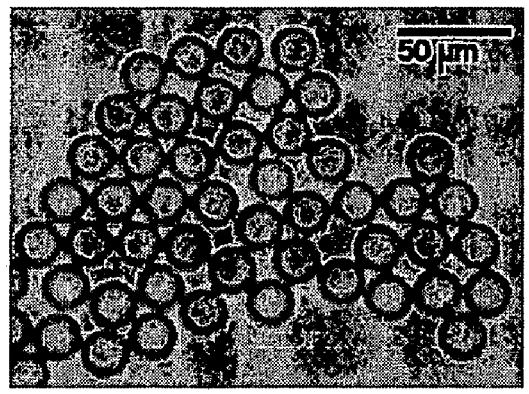
FIG. 8 is a set of photomicrographs of (a) 20 µm polymethacrylate particles, (b) 40 µm polymethacrylate particles, (c) Juniper Scopulorum pollen, and (d) Cottonwood pollen.
Figure 8B:
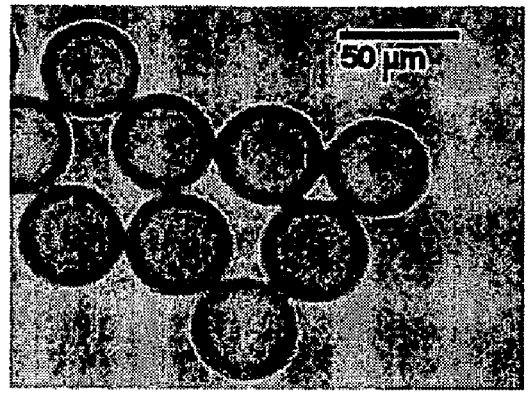
Figure 8C:
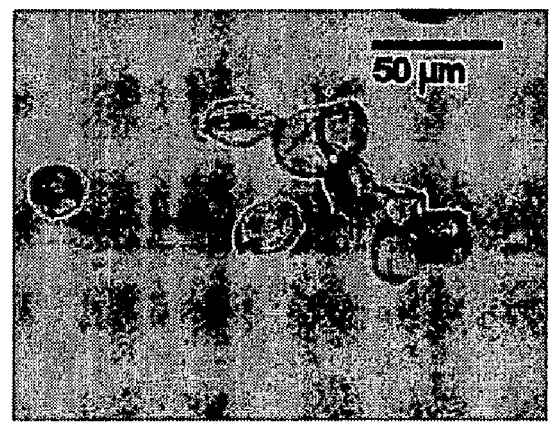
Figure 8D:
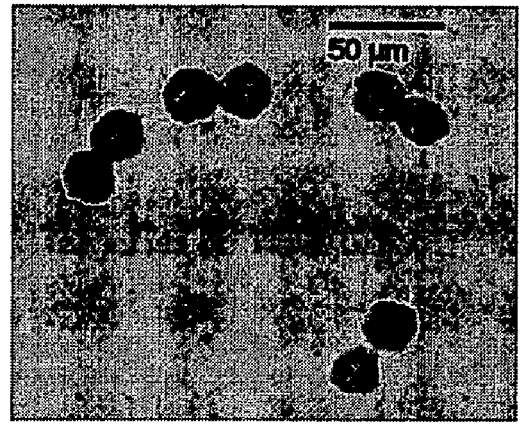

In one embodiment, a four-aperture sensor has four sampling resistors $R_{s1}$, $R_{s2}$, $R_{s3}$ and $R_{s4}$, across which four voltage measurements $V_{s1}$, $V_{s2}$, $V_{s3}$ and $V_{s4}$ are made. The overall measurement setup for the four-aperture sensor is electrically equivalent to the circuit shown in FIG. 7, where $R_{c1}$, $R_{c2}$, $R_{c3}$ and $R_{c4}$ are the resistances of the four microapertures. According to some embodiments, the four negative electrodes are electrically shorted in the central reservoir to ensure that each channel sees the same constant DC voltage $V_{cc}$. In this way, a variation in resistance in one microaperture does not cause voltage variation (i.e., crosstalk) in any other channel.

Example of Pollen Detection Embodiment:

One working example of the present invention is set forth as follows. Four types of micro-scale particles are chosen for a test of a multi-aperture sensor embodiment. They are polymethacrylate (PM) particles with diameters of 40 μm and 20 μm, Rocky Mountain Juniper (Juniper Scopulorum) pollen, and Cottonwood pollen. All particles are obtained from Sigma Aldrich, Inc. PM particles are chosen because they are commercially available and have well-characterized properties. The diameters of the pollen particles are determined using high-resolution optical microscopy, and range from 17.5 μm to 22.5 μm for the Juniper pollen and 20 μm for Cottonwood pollen. FIG. 8 shows photomicrographs of the four types of particles.

For experiments involving the polymethacrylate (PM) particles, 40 μm and 20 μm particle solutions can be prepared by diluting 0.1 mL of the original solution, which has 10% solid content, in 2 mL and 10 mL of deionized water, respectively. The estimated particle concentrations of the 40 μm and 20 μm particle solutions are approximately $1.2\times10^5$ mL$^{-1}$ and $2\times10^5$ mL$^{-1}$, respectively. For experiments involving Rocky Mountain Juniper pollen particles, a solution can be prepared by diluting 0.1 mL of the original pollen particles in 7 mL of deionized water.

In each example, 1 mL of the prepared particle solution is added to the central reservoir using a microsyringe. The liquid in the central reservoir is agitated to make sure that the particles are well dispersed. A gravity-induced pressure difference is created by placing the central reservoir at a higher level than the peripheral reservoirs. Pressure-driven flow forces the particle solution to move towards the peripheral reservoirs through the four sensing apertures.

The sampling resistor for each channel is $R_s=100$ kΩ, and the applied voltage across the electrodes of each channel is $V_{cc}=3$V. The entire measurement architecture is placed in a Faraday cage to reduce and/or control noise. As the particles pass through the microapertures, voltage pulses across all sampling resistors can be recorded simultaneously using, for example, a National Instruments NI-6220 data acquisition board. The voltages can be monitored in real time using, for example, LabView software with a sampling frequency of 20 kHz. The data obtained are converted to relative resistance change ($\delta R_c/R_c$) using Equation (1). This relative change is used to estimate the particle diameter (i.e., using Equation (3)). Particle concentration can be estimated by counting the number of resistive pulses during a selected time period.

Figure 9:
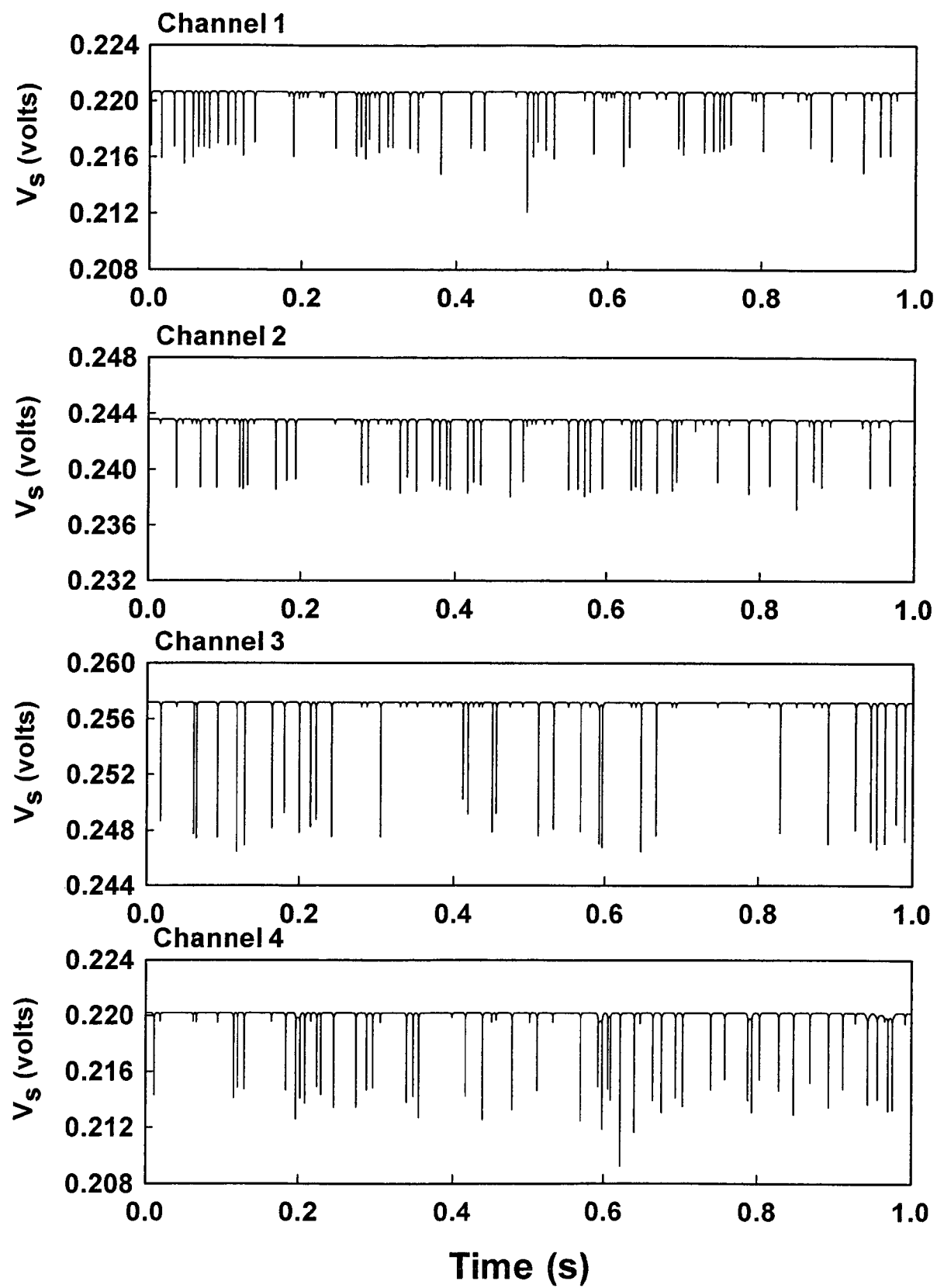
FIG. 9 is a set of four voltage traces obtained from four different sampling resistors in response to 40 µm PM particles.
Figure 10:
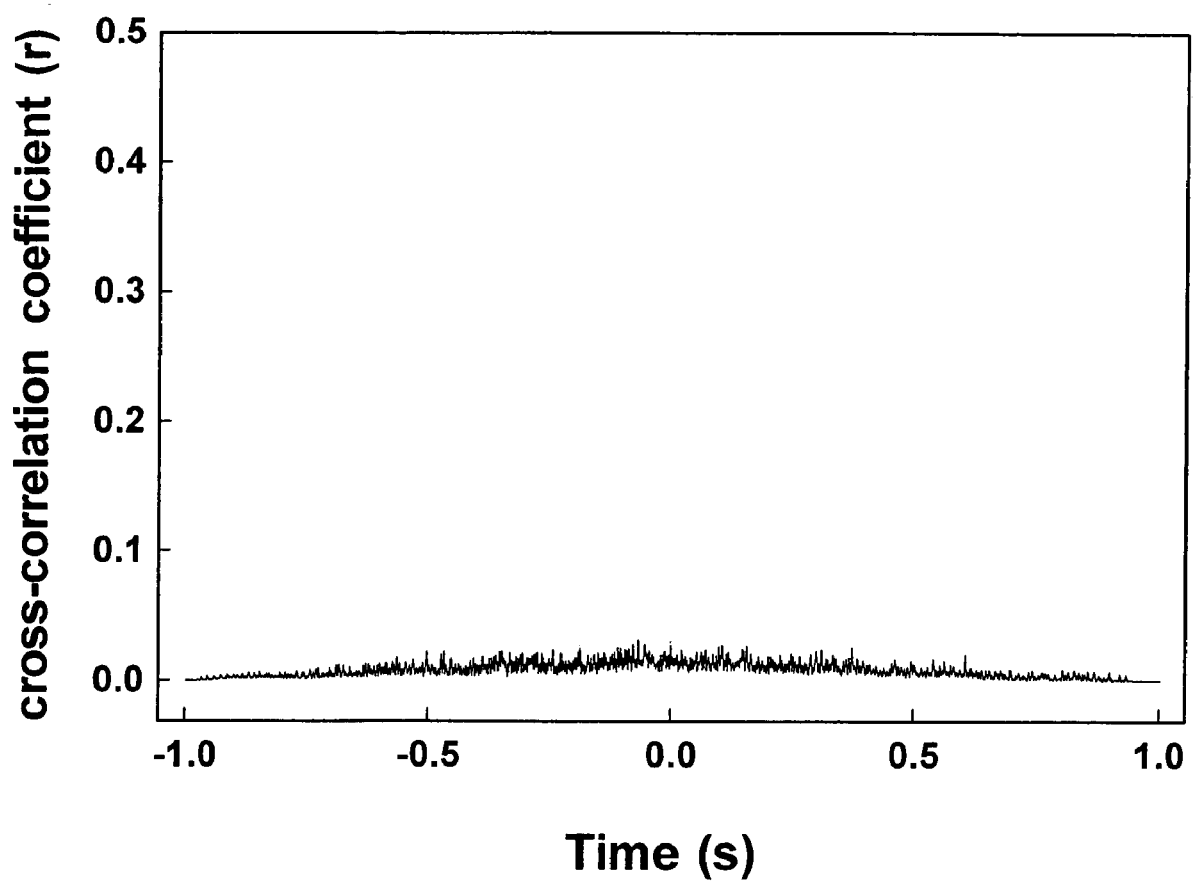
FIG. 10 is a graph showing typical results of a cross-correlation analysis performed on 40 µm PM particles.

Typical voltage traces resulting from the foregoing example are shown in FIG. 9. Pulses are recorded during a selected time period of one second. A typical result of a cross-correlation analysis performed on the signals from a pair of channels is shown in FIG. 10. The cross-correlation coefficients between channels are less than 5%, indicating negligible correlation among the pulses in different channels. This indicates that the four sensing apertures are able to simultaneously generate voltage pulses and count particles with negligible crosstalk among channels. Notably, different channels have different base voltages ($V_s$). This is primarily because the base resistances of the four microapertures ($R_{c1}$, $R_{c2}$, $R_{c3}$ and $R_{c4}$) differ due to fabrication artifacts.

Figure 11:
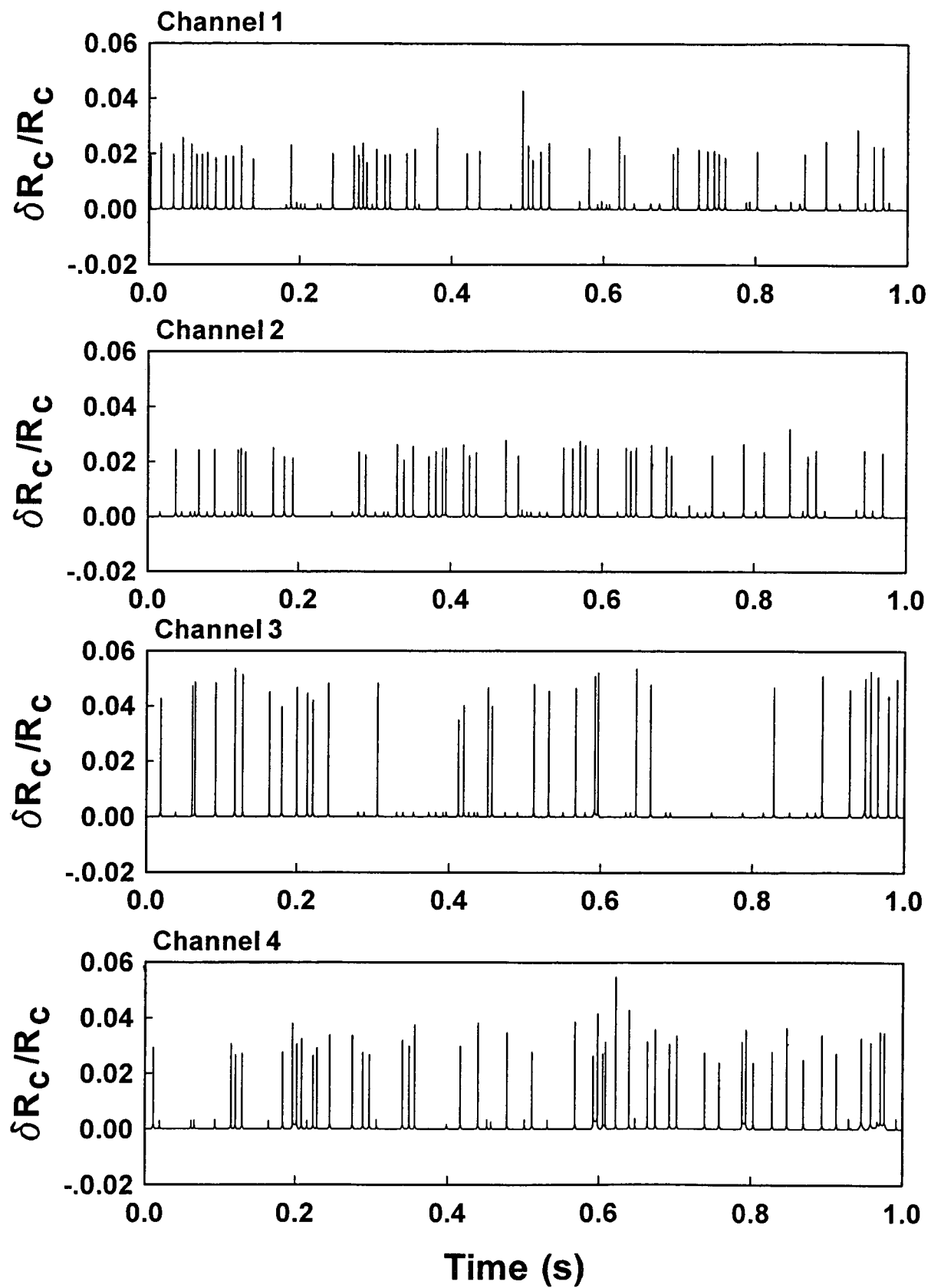
FIG. 11 is a set of four plots showing relative resistance of four sensing microapertures as a function of time, wherein each pulse corresponds to a single particle.
Figure 12:
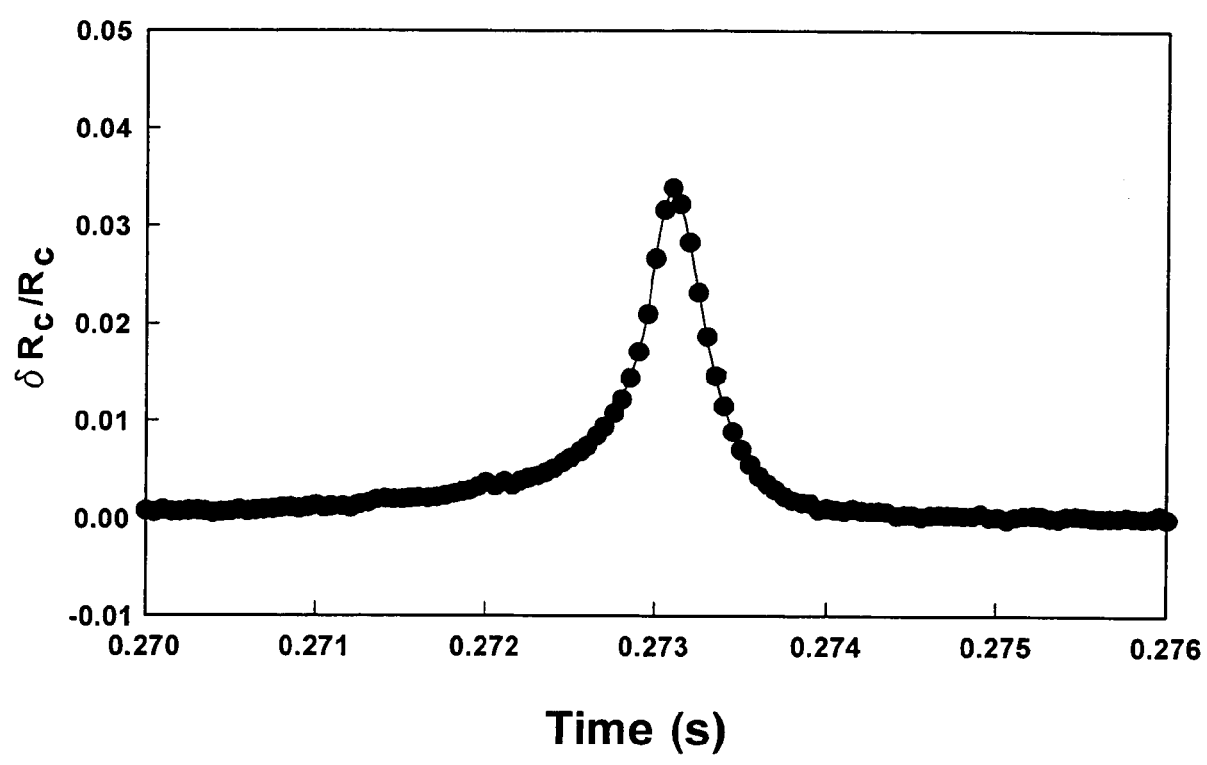
FIG. 12 is a typical resistive pulse resulting from a 40 μm PM particle passing through a microaperture.

The ratio of the resistance change ($\delta R_c/R_c$) for each microaperture, calculated using Equation (1), is plotted as a function of time in FIG. 11. FIG. 12 shows a more detailed view of a typical pulse for a 40 μm polymethacrylate particle from FIG. 11. It can be seen that the duration of the pulse due to the particle passing through the aperture is about 2 ms. Hence the average speed of a particle traveling through the channel is approximately 0.05 ms$^{-1}$. This is about the same as the velocity of the fluid flow. The average relative change in resistance is used to calibrate the length of each aperture using Equation (2). This calculation assumes that the aperture diameter measurement is accurate. The calibration results are shown in Table 3.

TABLE 3

| | Aperture 1 | Aperture 2 | Aperture 3 | Aperture 4 |
|---|---|---|---|---|
| Calibrated Length (L) | 173 μm | 153 μm | 118 μm | 127 μm |

Figure 13:
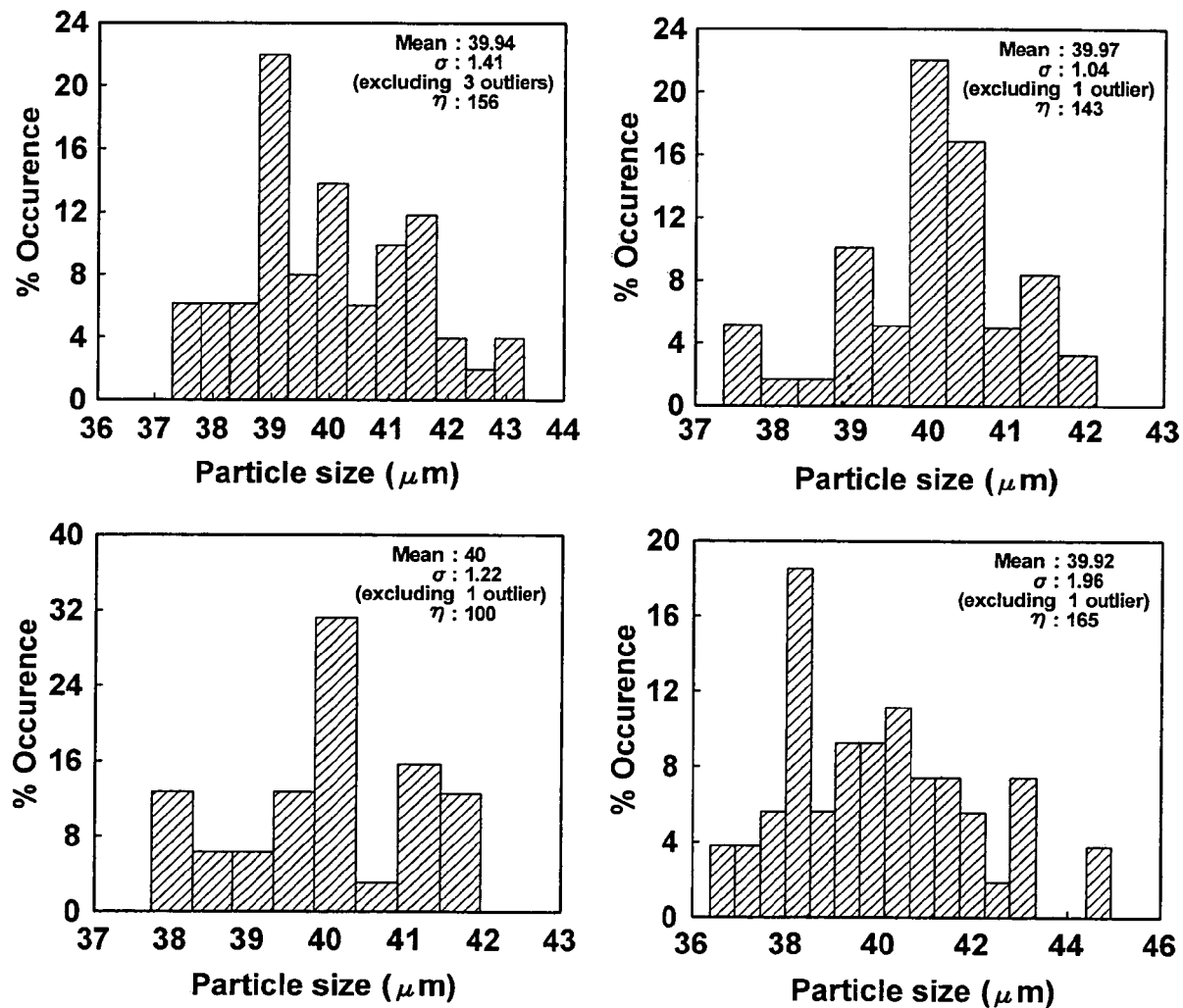
FIG. 13 is a set of four histograms showing particle size data obtained from each of four channels of the four-channel embodiment.

The calibrated aperture length can be used to calculate particle diameter using Equation (3). FIG. 13 shows a histogram of estimated particle size, along with the average size, standard deviation (σ) and number of particles (n) for each channel. The estimated particle diameters lie between about 37.28 μm and 43.25 μm (39.94±1.41 μm) for channel 1, between about 37.73 μm and 42.06 μm (39.97±1.04 μm) for channel 2, between about 37.78 μm and 41.9 μm (40±1.22 μm) for channel 3 and between about 36.44 μm and 44.92 μm (39.92±1.96 μm) for channel 4. The manufacturer specifies the actual diameter of the particles to be 40±0.8 μm. The measurement error in particle size is approximately within the overall uncertainty error range. The differences are likely due to the uncertainty of the microaperture dimension, electronic noise and the off-axis position when a particle passes through the microaperture.

The concentration of the particles in the four channels can be calculated from the number of peaks during a one second period as shown in FIG. 11. According to this example, the concentrations are found to be $1.09\times10^5$ mL$^{-1}$, $0.95\times10^5$ mL$^{-1}$, $1.04\times10^5$ mL$^{-1}$ and $1.12\times10^5$ mL$^{-1}$ for channels 1, 2, 3 and 4, respectively. The measured particle concentration in each channel is slightly lower than the estimated particle concentration, which is about $1.2\times10^5$ mL$^{-1}$. This is possibly because some PM particles are deposited onto the substrate during the experiments.

Figure 14:
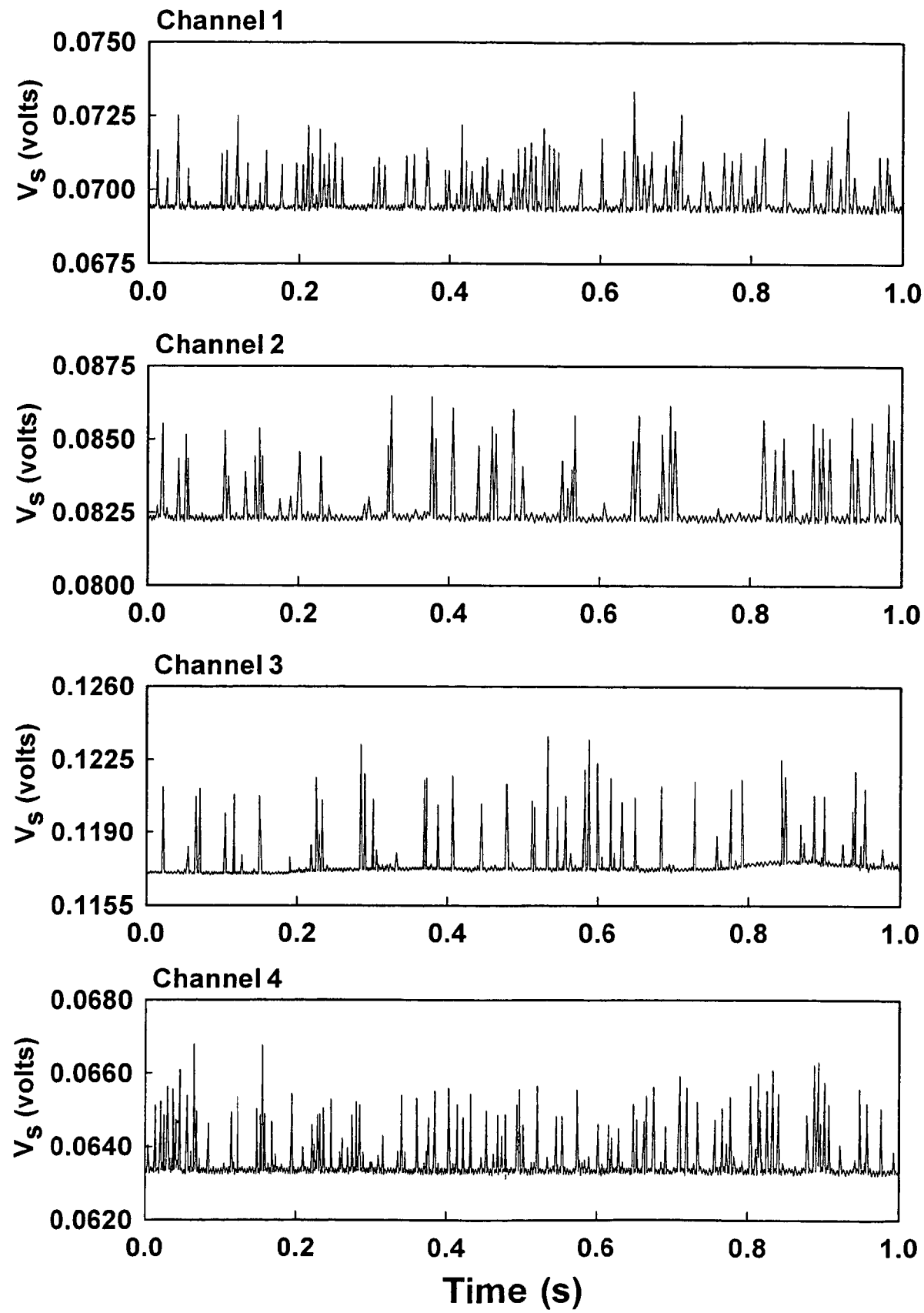
FIG. 14 is a set of four voltage traces obtained from each of the four sampling resistors and shows the voltage response due to Juniper pollen particles.
Figure 15:
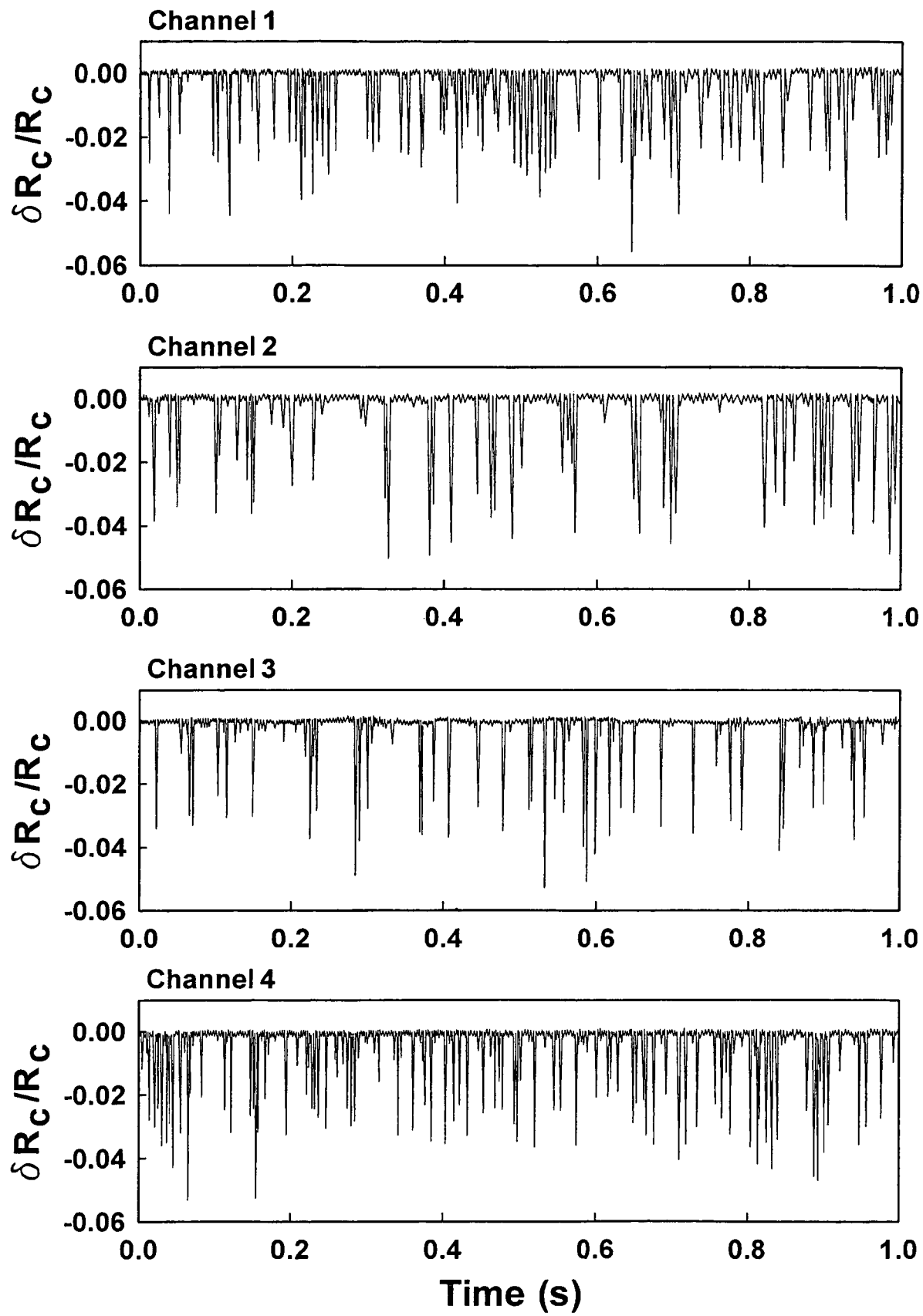
FIG. 15 is a set of four plots of the relative resistance due to Juniper pollen particles.
Figure 16:
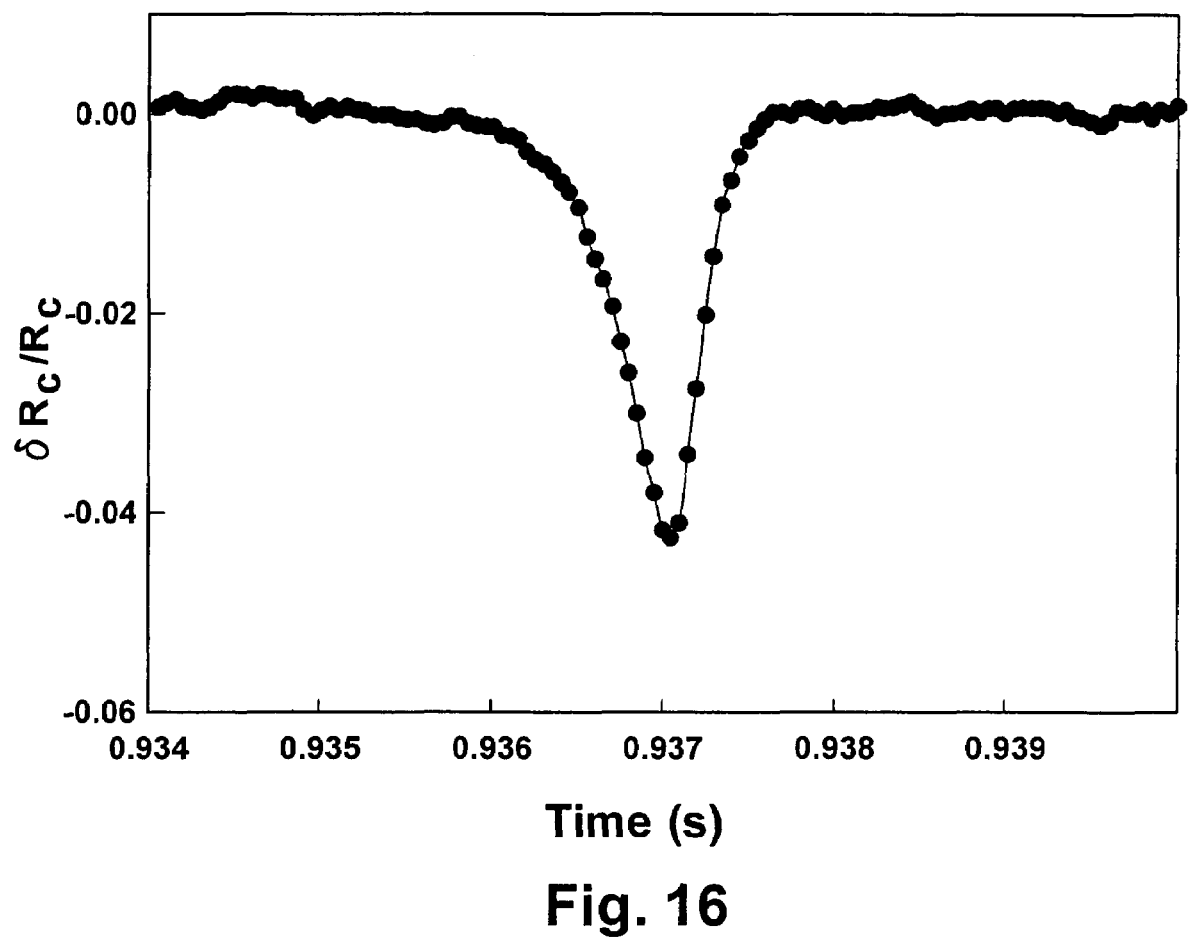
FIG. 16 is a typical resistive pulse resulting from a Juniper pollen particle.

Typical voltage traces with pulses are shown in FIG. 14, and are recorded over a time period of one second. It can be observed that the polarity of the voltage pulses when a pollen particle passes through the microaperture is opposite to that caused by a polymethacrylate particle (FIG. 9). As is the case for the PM particle experiments, the cross-correlation analysis shows negligible crosstalk among channels. The measured voltages are converted to relative changes in aperture resistance as shown in FIG. 15. The downward resistance pulse corresponds to a decrease in the resistance of the microaperture when a pollen particle passes through the aperture. A typical pulse for a Juniper pollen particle taken from FIG. 15 is shown in FIG. 16.

This phenomenon indicates that a particle affects the microaperture resistance in two competing ways. First, it displaces electrolyte solution in the microaperture, thereby reducing the number of free ions inside the microaperture, which leads to an increase in resistance. Second, if it has a surface charge, it brings additional charges into the microaperture, which leads to a decrease in resistance. According to the results from this example, the pollen particles have high surface charge, while the PM particles are only slightly charged. When the surface charge is high and the concentration of ions in the electrolyte solution is low, as is the case for pollen particles in this example, the second factor is dominant, and the overall effect of a pollen particle passing through a microaperture is a downward resistive pulse. This phenomenon can be used to differentiate pollen particles from other only slightly charged particles. It is also possible to measure pollen particle size using electrolyte solution of high concentration, so that the particle size plays the dominant role in the size of the resistive pulse.

In order to further demonstrate that this embodiment can be used to differentiate various particles, two additional particles, 20 μm polymethacrylate particles and Cottonwood pollen, are tested using a single Coulter cell (channel 1 with the 110 μm aperture). These two particles are chosen because they are similar in size to Juniper pollen but may differ in surface properties.

Figure 17A:
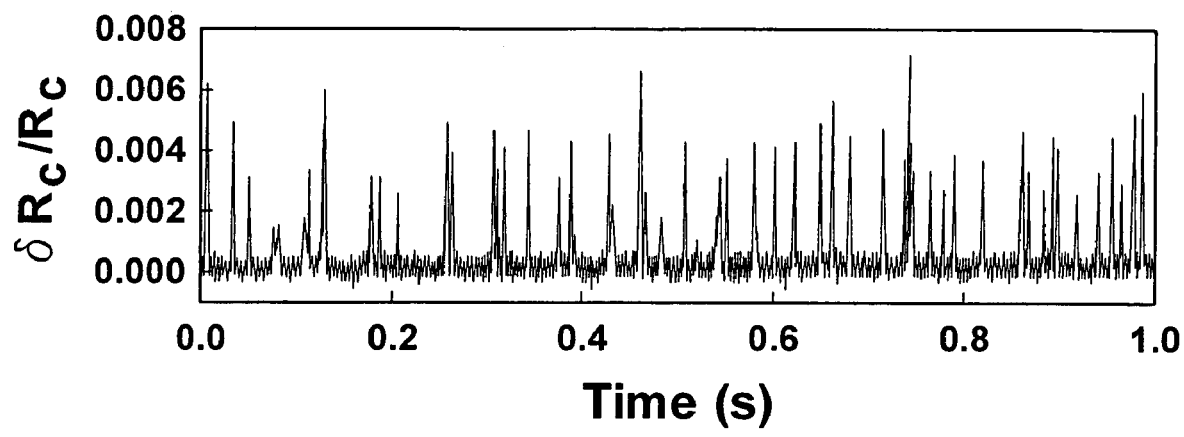
FIG. 17 is a pair of plots showing the relative resistance pulses from a single channel embodiment due to (a) 20 μm PM particles, and (b) cottonwood pollen particles.
Figure 17B:
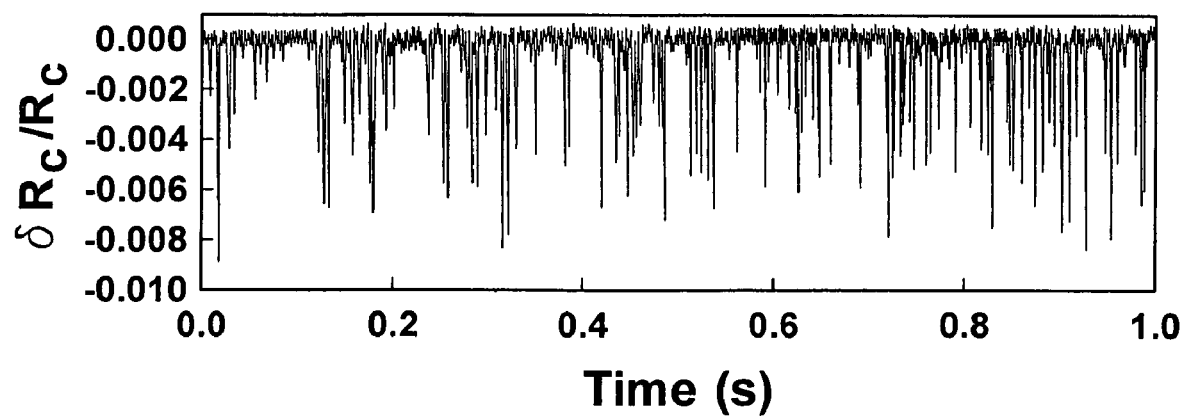

Typical traces of resistive pulses are shown in FIGS. 17(a) and (b). These traces show resistive pulses that are calculated from voltage signals recorded over a one second period. The traces correspond to the 20 μm PM particles, and the Cottonwood pollen. The particle diameters are calculated from the resistive pulse data shown in FIG. 17(a). Using the calibrated aperture length of 173 μm, the statistical analysis shows that the estimated particle diameter is 22.46±2.1 μm. The difference between the calculated and the actual particle diameter (20 μm±0.5 μm) can be minimized by calibrating both the aperture diameter and aperture length using a number of quasi-monodisperse particles of standard sizes. While the estimated particle diameters appear to have a larger divergence about the average than that specified by the manufacturer (20±0.5 μm), the measurement error is approximately within the overall uncertainty error range. The concentration of the 20 μm PM particles is calculated from the number of peaks during a period of one second. According to this example, the concentration is calculated to be $1.91 \times 10^5$ mL$^{-1}$, compared to the original concentration estimate of $2 \times 10^5$ mL$^{-1}$.

Like Juniper pollen, Cottonwood pollen particles generate downward resistive pulses (a decrease in resistance) when they pass through the microaperture (FIG. 17(d)). However, the resistive pulse height (relative to the base resistance of microaperture) generated by Cottonwood pollen (0.478%±0.226%) is considerably lower than that of the Juniper pollen (2.73%±0.99%). While not wishing to be bound to any one theory, this phenomenon may be attributed to a difference in surface charge. The influence of aperture geometry can be eliminated by normalizing the relative resistive pulses for 20 μm and 40 μm PM particles, Juniper pollen, and cottonwood pollen using the following equation:

$$(\delta R_c / R_c)_{normalized} = (\delta R_c / R_c) \cdot \left( \frac{L'D^2}{\frac{D^2}{2L^2} + \frac{1}{\sqrt{1 + \left(\frac{D}{L}\right)^2}}} \right) \quad (4)$$

A scatter plot of normalized $\delta R_c/R_c$ for the four particles is shown in FIG. 18. It indicates that the four tested particles can be identified in a mixture by using the polarity and magnitude of the resistive pulses. While not wishing to be bound to any one theory, the large variation in resistive pulses of Juniper tree pollen may be due to a variation in particle size and shape, and in surface charge.

The results for both the PM particle and pollen experiments indicate that this instrument is capable of counting particles through the four microapertures simultaneously. In contrast to a single channel Coulter counter, the counting efficiency is improved by a factor of approximately three. This counting efficiency can be further improved by integrating more sensing apertures in a micromachined device. The noise in the sensed voltages averages to about 0.1 mV. Thus, this embodiment should be able to detect particles that produce pulses larger than this noise level. Accordingly, this embodiment is capable of detecting particles with diameters larger than approximately 8.2 μm, or 6.9% of the microaperture diameter. We expect that the sensitivity can be improved by using better shielding and electronics to reduce the noise level.

The foregoing example demonstrates that some embodiments of the present invention can be used to distinguish between kinds of particles and to count pollen and other particles with significantly improved efficiency.

According to this example, uncertainty analysis is carried out using the methods of Moffat, Kline and Coleman and Steele. There are three sources of uncertainty in the estimation of the particle size. The first source is due to uncertainty in measurement of the microaperture diameter and in the calibration procedure used to determine microaperture length. Due to the fabrication process used to make the microapertures, the microapertures vary in size. The uncertainty in measuring the diameter is ±10%. The calibration process for determining the length presumes that the measured diameter is correct. The uncertainty in diameter causes a maximum uncertainty of ±42.5% for microaperture length. Together, the uncertainties in aperture diameter and length contribute a maximum of ±12.1% uncertainty in particle size evaluation. Note that this source of uncertainty systematically alters the estimates of the particle diameters and can be reduced by calibrating the sensor using quasi-monodisperse particles in a number of standard sizes. Taking data using two different particle sizes, for example, allows the practitioner to solve for both the effective diameter and the effective length of a microaperture, thereby reducing uncertainty for both parameters.

The second source of uncertainty is due to fluctuations in the output voltage, which are about ±0.05 mV at base voltage levels of 0.22 V. These fluctuations could be due to either flow unsteadiness or the measurement electronics, and appear to have no systematic trend. According to Equation (3), this uncertainty contributes to an uncertainty of ±0.58% and ±4.5% in particle diameter estimation for 40 μm and 20 μm polymethacrylate particles, respectively.

The third source of uncertainty is due to particles passing off-axis through the aperture. Given the shape of the pulses observed, we expect a maximum increase of about 10% in the measured response. This corresponds to an uncertainty of ±3.3% in particle size. Combining the three uncertainty sources, the uncertainties of particle size estimation are ±12.5% and ±13.2% for 40 μm and 20 μm polymethacrylate particles, respectively. The foregoing results show that the measurement error of the counter is well within this uncertainty error range.

II. Label-Free Resistive Pulse Sensor Embodiments:

FIG. 5 shows general structure that is consistent with the following embodiment. Similar to the previous embodiment, this embodiment comprises four peripheral reservoirs and a central reservoir. Each peripheral reservoir is connected to the central reservoirs through a mini channel. A microchannel, fabricated on a polymer membrane, is positioned in the middle of each mini channel and used for particle sensing.

Figure 18A:
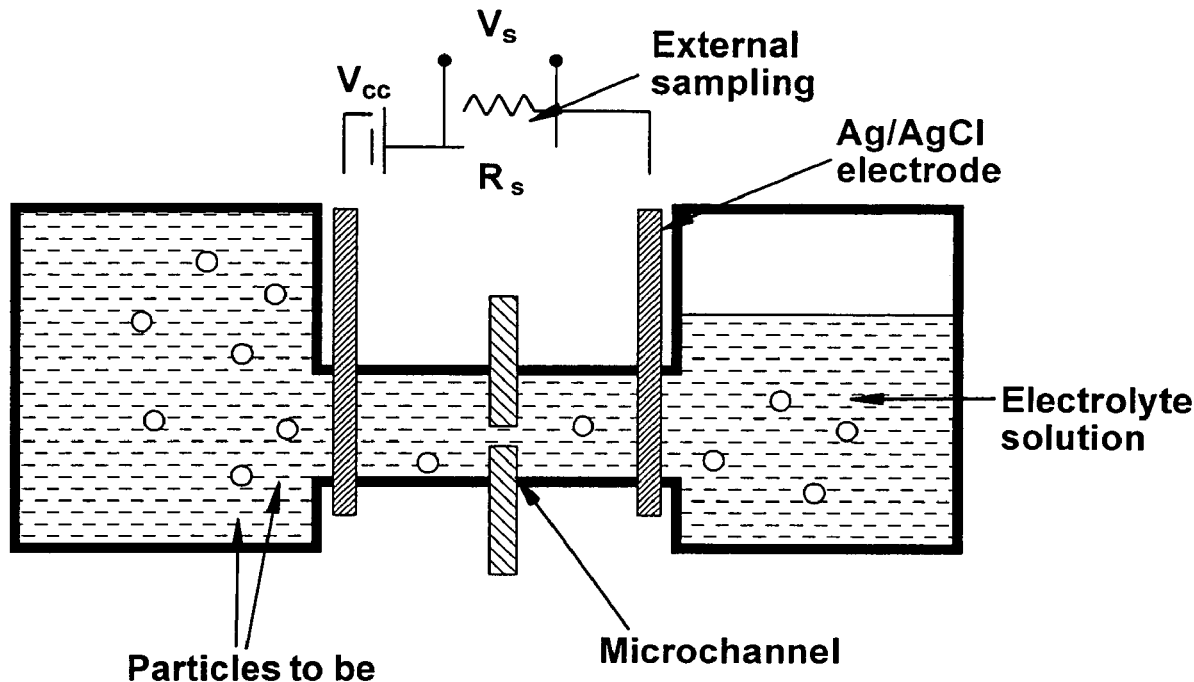
FIG. 18 is a pair of schematics showing (a) a front view of a single channel embodiment; and (b) a magnified view of a single channel embodiment.
Figure 18B:
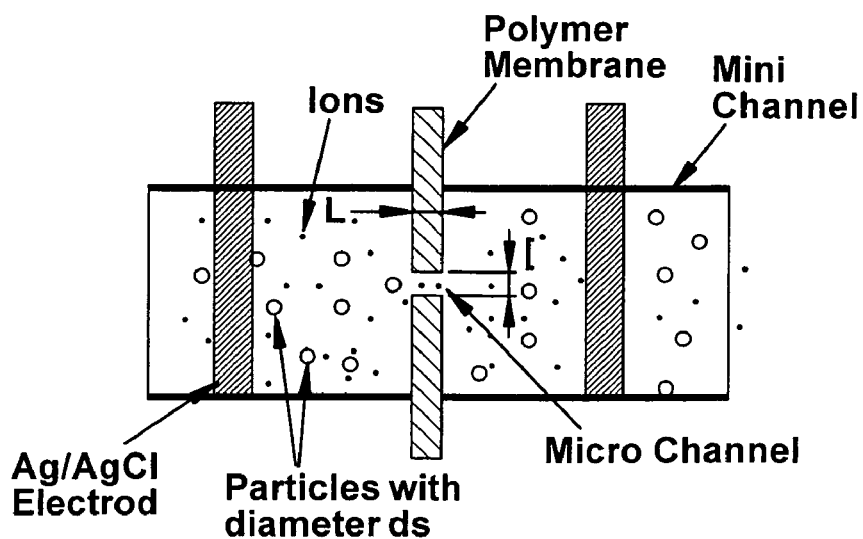

FIG. 18(a) shows the sectioned schematic front view of a single sensing channel along with the measurement setup. $R_s$ is a known external sampling resistor. The Ag/AgCl electrodes placed on both sides of the membrane is used for applying a constant DC voltage $V_{cc}$. FIG. 18(b) shows a blow-up drawing of the mini-channel, microchannel and electrodes.

Figure 19A:
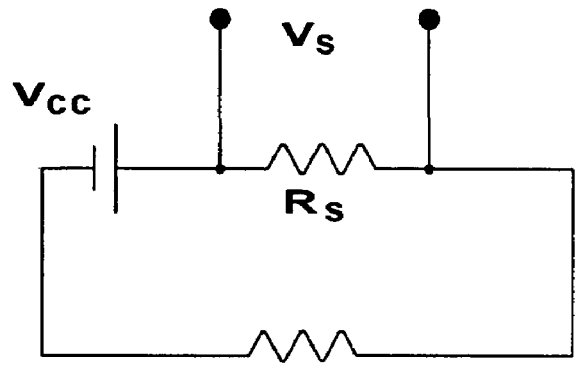
FIG. 19 is a pair of electrical equivalent circuits of (a) a single channel embodiment, and (b) a four channel embodiment.
Figure 19B:
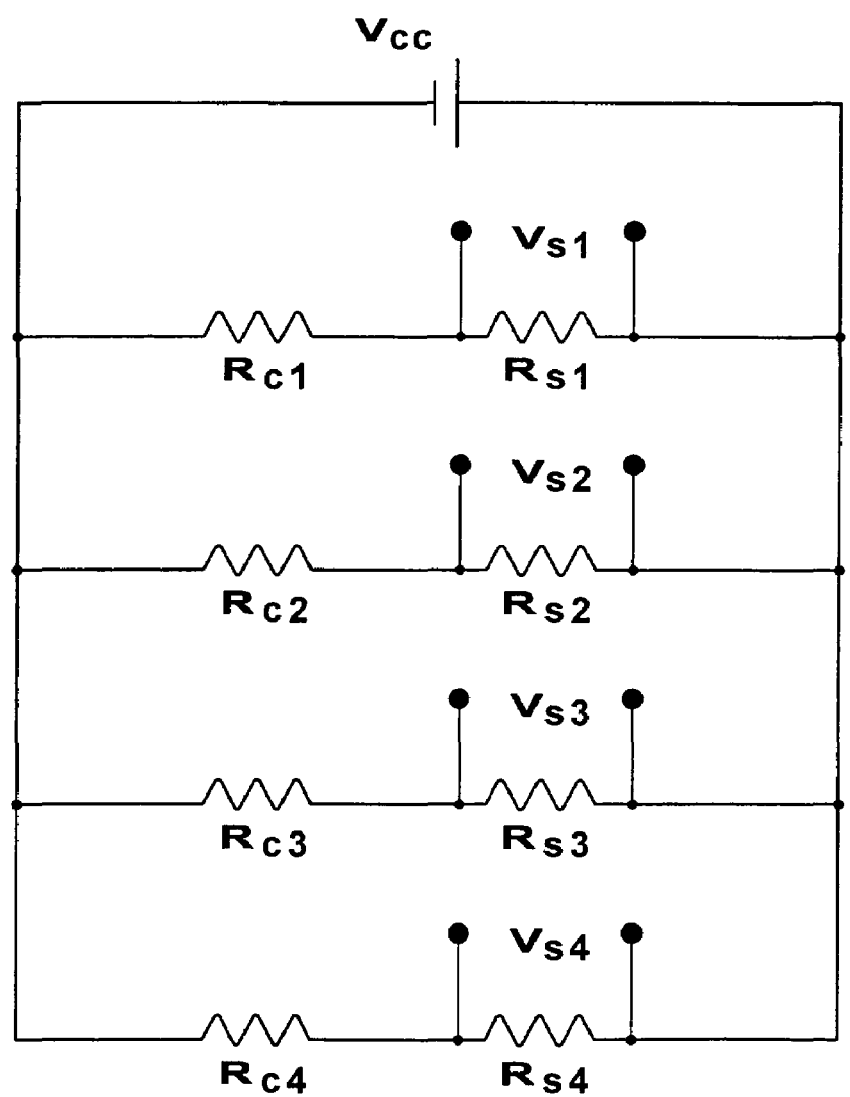

The measurement circuit for one sensing channel is equivalent to the circuit in FIG. 19(a), where $R_c$ is the resistance of the electrolyte-filled microchannel. $R_c$ has a variation $\delta R_c$ when a particle passes through the channel, because it displaces some of the electrolyte solution in the microchannel. This causes a change in the measured voltage $V_s$ across the sampling resistor $R_s$. From the circuit model in FIG. 19(a), the relative change in the resistance of the microchannel is given by Equation (1), where $\delta R_c$ is the change in channel resistance when a particle passes through the microchannel, $V_s$ is the voltage measured across the sampling resistor when the channel is filled only with electrolyte solution and $V_s'$ is the peak voltage measured across the sampling resistor as a particle passes through the microchannel.

For a microchannel with length L and diameter D (see FIG. 18(b)), the change in resistance as a particle passes through it is given by Equation (2). Thus, the particle diameter can be calculated from the relative change in resistance based on Equation (3).

According to one very specific example, the central reservoir and half of each of the four mini channels can be fabricated by drilling holes in a polymethyl methacrylate (PM) block. In each of four additional PM blocks, holes are drilled to form the other half of a mini channel and a peripheral reservoir. According to this example, the central reservoir is 12 mm in diameter and 10 mm deep. Each peripheral reservoir is 10 mm in diameter and 10 mm deep. The mini channel is 4 mm in diameter. After the holes are drilled, the PM blocks are cleaned with isopropanol and sonicated in an ultrasound bath. The microchannels are fabricated by carefully piercing four polymer membranes with a heated micro needle. The membranes are inspected under a high precision microscope and the diameters of the microchannels are measured to be between 120 μm and 130 μm, as shown in Table 4. The thickness of the membrane (and therefore the length of each microchannel) is measured to be approximately 100 μm.

TABLE 4

|  | Channel 1 | Channel 2 | Channel 3 | Channel 4 |
|---|---|---|---|---|
| Length L | 100 μm | 100 μm | 100 μm | 100 μm |
| Diameter D | 120 μm | 120 μm | 130 μm | 120 μm |

To assemble the device, the PM block with the central reservoir and one of the PM blocks with a peripheral reservoir are picked, and epoxy is applied on the mini channel side of the two blocks. A membrane is placed between the two blocks and is carefully aligned so that its microchannel is centered between the two halves of the mini channel. The blocks are then clamped together and kept about two to five hours, or until the two blocks and the membrane are firmly attached together. A pair of 1 mm holes, located 5 mm away from each membrane on both sides, is drilled on the PM blocks. The 1 mm diameter Ag/AgCl electrodes are placed on both sides of the membrane through the 1 mm holes. Then epoxy is applied to fix the electrodes and seal the mini channel. The same procedure is repeated for the other three peripheral blocks to form a four-channel sensor.

Figure 20A:
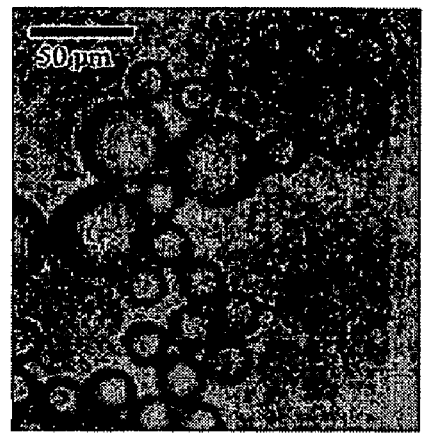
FIG. 20 is a set of three photomicrographs of (a) 20 μm PM particles and 40 μm PM particles, (b) cottonwood pollen, and (c) Juniper Scopulorum pollen.
Figure 20B:
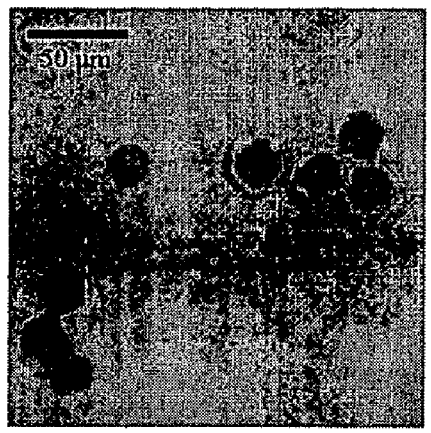
Figure 20C:
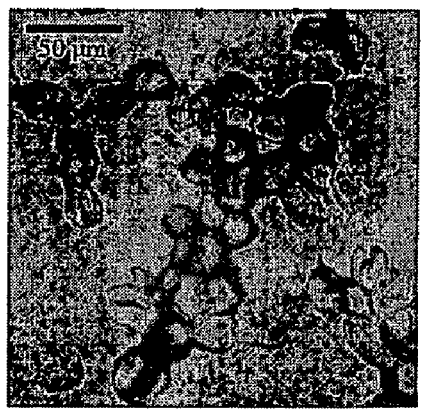

Four microparticles, polymethacrylate particles with well-characterized diameters of 20 μm (20 μm±0.5 μm) and 40 μm (40 μm±0.8 μm) (Sigma Aldrich Inc.), Rocky Mountain Juniper (Juniper Scopulorum) tree pollens (Sigma Aldrich Inc.) and Populus deltidoes/Eastern Cottonwood pollens (Sigma Aldrich Inc.) are chosen for testing. These particles are chosen because they are commercially available and have well-characterized properties. The diameters of pollen particles are determined using high resolution optical microscopy. The cotton pollen had a diameter of about 20 μm. The Juniper tree pollen is egg-shaped and its diameter ranged from 17 μm to 23 μm. FIG. 20(a) shows pictures of the 20 μm and 40 μm polymethacrylate particles. FIGS. 20(b) and (c) shows the pictures of Cottonwood and Juniper tree pollen respectively taken with the microscope.

Four particle solutions are prepared before the experiments. 40 μm polymethacrylate particle solutions are prepared by diluting 0.1 mL original particle solution, which has 10% solid content, in 2 mL of deionized water. The yield particle concentration of 40 μm solution is approximately $1.2 \times 10^5$ mL$^{-1}$. 20 μm polymethacrylate particle solutions are prepared by diluting 0.1 mL original particle solution (10% solid content) in 7 mL of deionized water and the yield particle concentration of 20 μm solution is approximately $2.8 \times 10^5$ mL$^{-1}$. For Cottonwood and Juniper tree pollen particles, the particle solutions are formed by diluting 0.1 mL of the original pollen particle solutions (10% solid content) in 7 mL of deionized water.

The prepared particle solution is injected into the peripheral reservoirs separately using a micro syringe. Juniper tree pollen particles, Cottonwood particles, 40 μm and 20 μm polymethacrylate particles are loaded into channels 1, 2, 3 and 4 respectively. The liquid in each peripheral reservoir is agitated to make sure that the particles are well dispersed. A pressure difference is formed by setting a level difference between the peripheral reservoirs and central reservoir. The particle solutions are driven to move from the peripheral reservoirs towards the central reservoir, which now act as a collecting/sink reservoir.

The entire measurement setup is placed in a Faraday cage to reduce noise. The applied electric potential across the pair of electrodes of each channel is $V_{cc}=3$ V. The sampling resistor for each channel is 100 kΩ. As the particles passes through the microchannels, voltage pulses across all sampling resistors are recorded simultaneously using a National Instruments NI-6220 data acquisition board. The voltages are monitored in real-time using LabView software with a sampling frequency of 20 KHz. The data obtained are converted to relative resistance change ($\delta R_c/R_c$) using Equation (1). The relative change is used to estimate the particle diameter (using Equation (3)) and particle concentration.

Figures 21A, 21B:
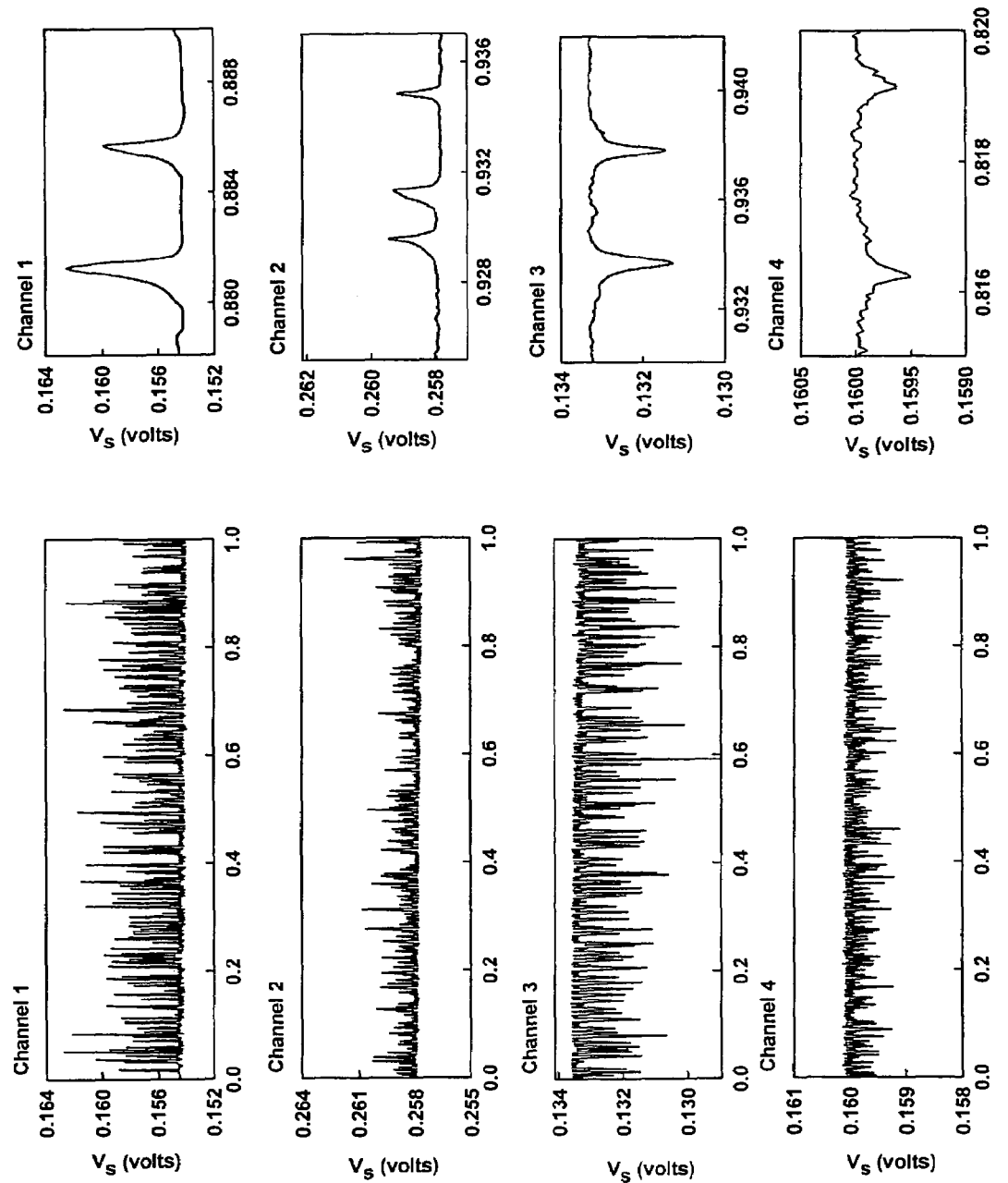
FIG. 21 is a set of plots showing (a) data from four sampling resistors, and (b) magnified voltage pulses.
Figure 22B:
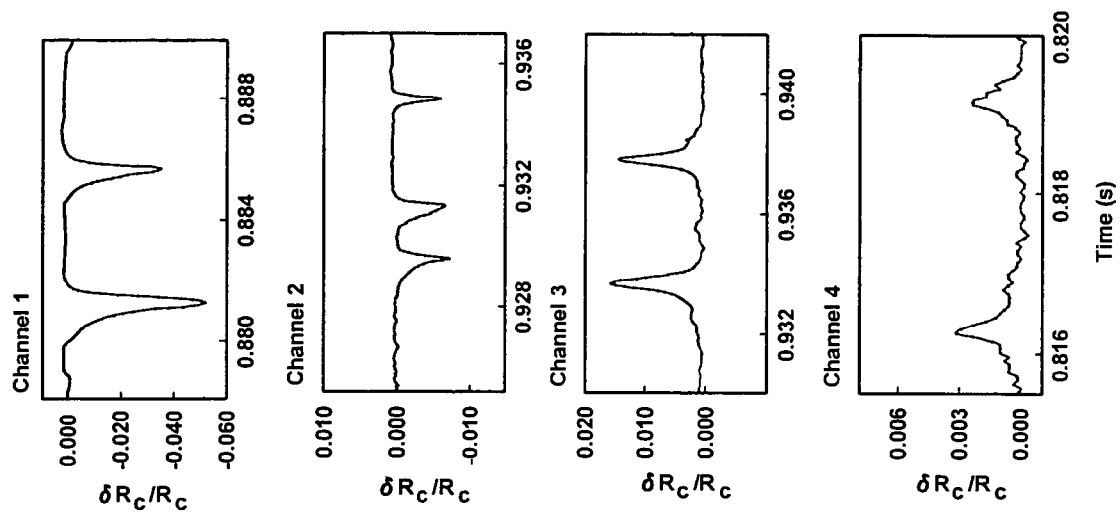
FIG. 22 is a set of plots showing (a) the relative resistance of each channel, and (b) magnified resistive pulses for each channel.

Example of Label-Free High-Throughput Resistive-Pulse Sensing:

The typical measurement results of voltage traces across the four sampling resistors during a selected period of time are shown in FIG. 21(a). A few magnified pulses showing more details of the pulse shape are shown in FIG. 21(b). It is obvious that the voltage pulses appear in random sequence. The cross correlation analysis is performed between the signals from two sensing channels at a time. We found that the cross correlation coefficients are all less than 5%, indicating there is no correlation among the pulses of different channels. This implies that the four sensing channels can simultaneously detect and count particles without crosstalk among the channels. Note that the difference in the base voltage ($V_s$) is due to the base resistance difference ($R_{c1}$, $R_{c2}$, $R_{c3}$, $R_{c4}$) among microchannels because of the fabrication variation. The particle travel velocity in the microchannel is estimated by measuring the pulse width (i.e., time one particle took to pass the microchannel) and the length of the microchannel, which is used to estimate the particle concentration later. Some resistive pulses shown in FIGS. 21(b) and 22(b) have a steeper slope when the particles exit the microchannel than they enter the microchannel. This may be a result of the particles entering the microchannel at the center and exiting the microchannel near the channel wall at an angle.

Figure 22A:
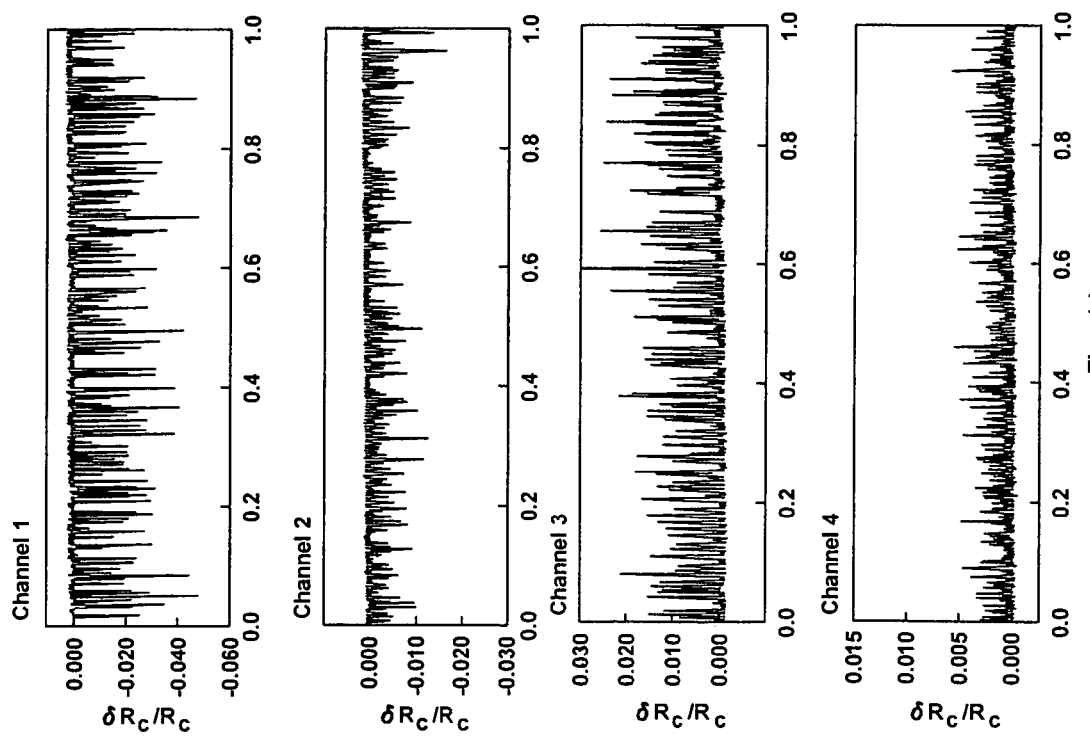

The voltage pulses of each microchannel are converted to the ratio of the resistance change using equation. The results are plotted in FIG. 22(a) as a function of time, along with a few magnified resistive pulses showing more details in FIG. 22(b). It is obvious that the four types of particles can be differentiated based on the direction (downward or upward) and height of resistive pulses.

Figure 23A:
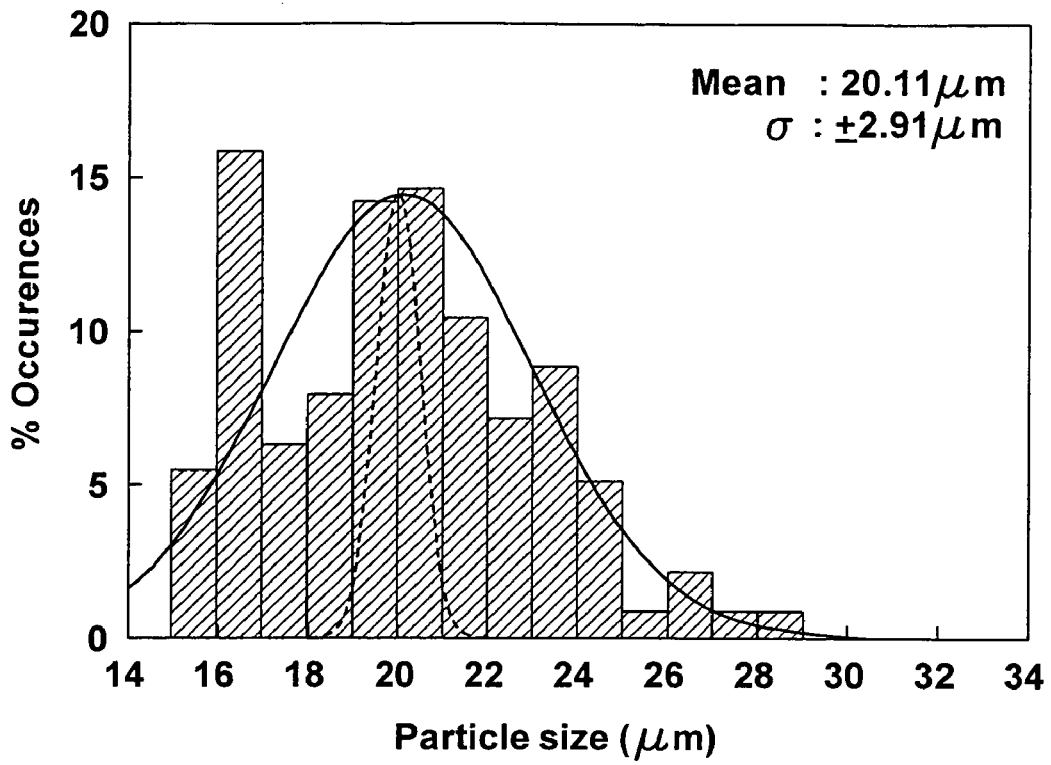
FIG. 23 is a pair of histograms showing the estimated particle size of (a) a 40 μm particle, and (b) a 20 μm particle.
Figure 23B:
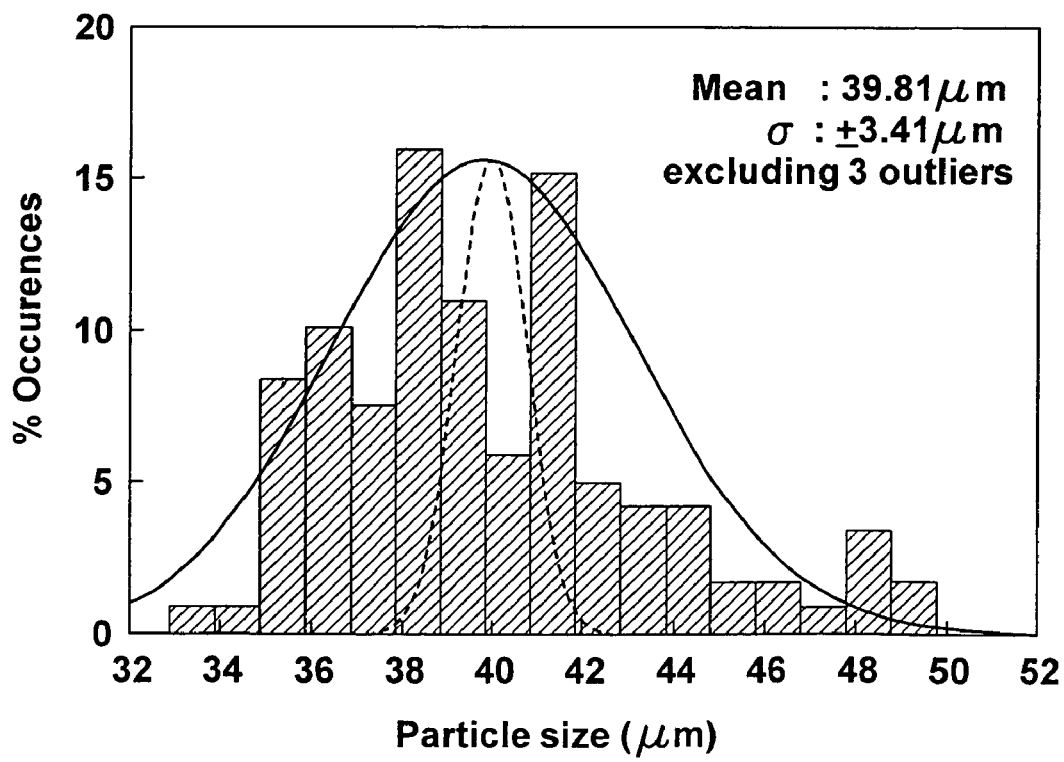

The relative changes of resistance in channels 3 and 4 are used to calculate the polymethacrylate particle diameters using Equation (3). FIG. 23 shows a histogram of the estimated particle size, along with the average size and standard deviation in size, for channels 3 and 4. The estimated particle diameters lie in the range of about 32.89 to 48.96 μm (average 39.81 μm, σ=±3.41 μm) for channel 3, about 15.68 to 28.18

μm (average 20.11 μm, σ=±2.91 μm) for channel 2. The estimated particle size appears to have relatively larger divergence compared to the actual diameter of the polymethacrylate particles specified by the manufacturer, which are 40±0.8 μm and 20±0.5 μm. This is possibly because of the uncertainties in microchannel dimension, electronic noise and the off-axis position when particles pass through the microchannel. The measurement error in the particle size is approximately within the overall uncertainty error range. From the number of peaks appearing in channels 3 and 4 during a period of one second, the concentrations of particles are calculated to be $1.33 \times 10^5$ mL$^{-1}$ (estimated actual concentration is $1.2 \times 10^5$ mL$^{-1}$), $2.46 \times 10^5$ mL$^{-1}$ (estimated actual concentration $2.8 \times 10^5$ mL$^{-1}$), respectively. The calculated concentrations from measured resistance pulses are in good agreement with the estimated actual concentrations. The slight difference is possibly because of the non-uniformity of particle distribution in the solution. The results show that the device is capable of counting polymethacrylate particles and determining their sizes accurately.

Figure 24A:
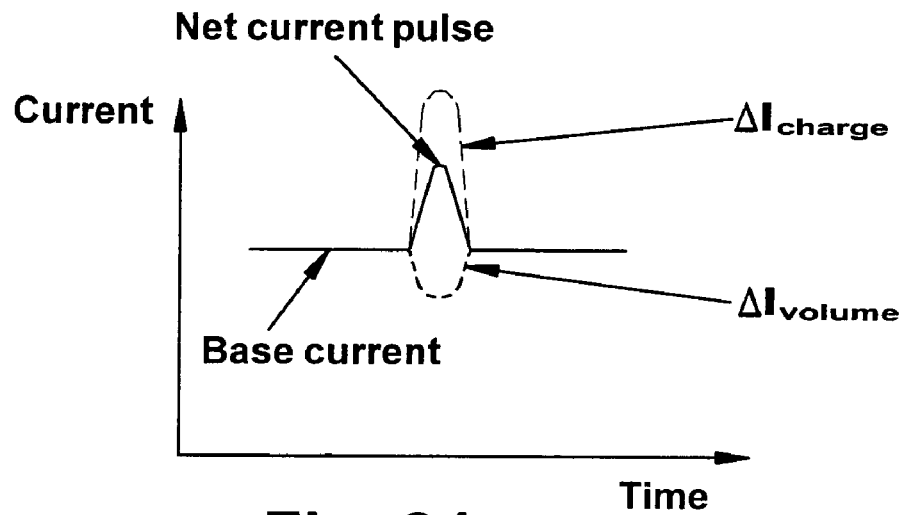
FIG. 24 is a set of drawings showing (a) a qualitative illustration of resistive pulse shape, (b) the result of a neutral particle entering a channel, and (c) the result of a charged particle entering a channel.
Figure 24B:
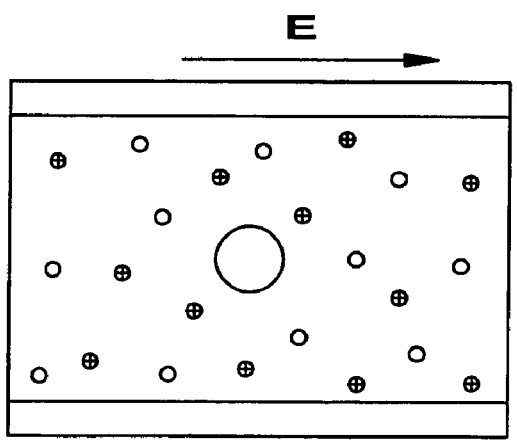
Figure 24C:
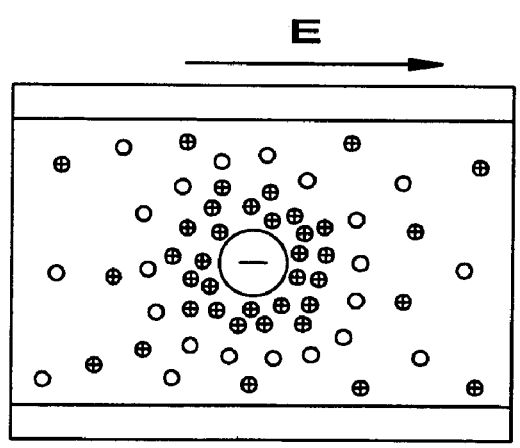

As shown in FIG. 22, in channels 1 and 2, the resistance pulses caused by Juniper pollens and Cottonwood pollens are all downward. This implies a decrease in the microchannel resistance when a pollen particle passed through the microchannel. This phenomenon can be explained in terms of the surface charge of particles. As illustrated in FIG. 24(*a*), a particle affects the ionic current in two competing ways: first, the particle physically displaces some of the electrolyte solution and reduces the amount of free ions inside the microchannel and hence the ion density σ. The ionic current across the microchannel can be written as:

$$I = \int_A \sigma \mu E \, dA \quad (5)$$

where μ is the mobility of the free ions, E is the applied electric field and A is the cross section area. Therefore the particle induces a decrease in ionic current ($\Delta I_{volume}$) as usually expected. Second, if the particle has high surface charge (see FIG. 24(*b*)), it induces excess ions in the microchannel owing to its high surface charge. Hence the ion density σ increases, leading to an increase in ionic current ($\Delta I_{charge}$). When the particle surface charge is high and the concentration of ions in the electrolyte solution is low, as is the case in the present example, the ionic current increase ($\Delta I_{charge}$) is dominant (FIG. 24(*c*)). The overall effect of a particle with high surface charge passing through a microchannel is an upward ionic current pulse (see FIG. 24(*a*)). Therefore, according to Ohm's Law, R=V/I (V is the applied voltage), a downward resistive pulse will occur. If the surface charge of a particle is negligible, $\Delta I_{charge}$ is negligible and an upward resistive pulse is generated. The results presented in this example suggest that pollen particles are highly charged, while polymethacrylate particles are slightly charged. While not wishing to be bound to any one theory, the height of downward resistive pulses could be explained by the surface charge of pollen particles. Furthermore, according to this example, the size of pollen particles can be measured in high concentration electrolyte solutions (e.g., 0.1 M KCl solution, for instance), because the induced charge density increase due to pollen is negligible at concentrations.

Figure 25:
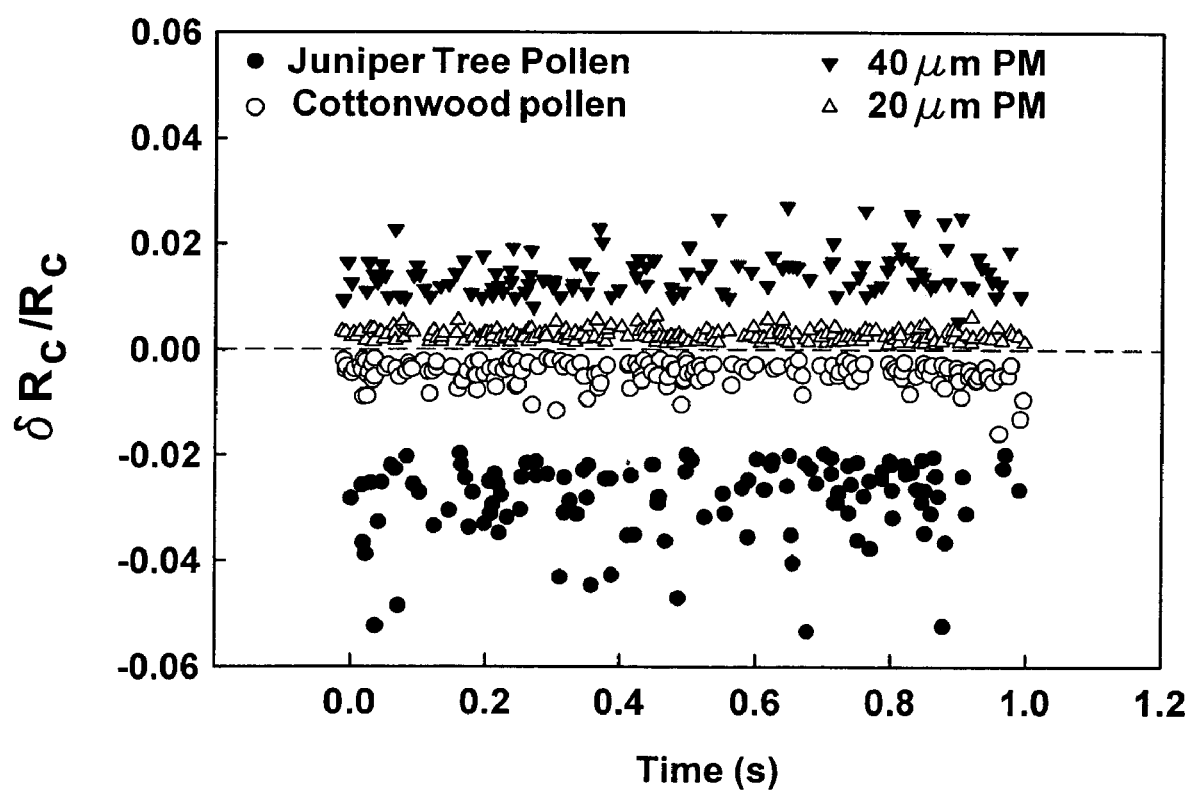
FIG. 25 is a scatter plot of the relative resistive pulse heights due to four different particles, i.e., 20 μm PM, 40 μm PM, cottonwood pollen, and Juniper pollen.

As demonstrated by this example, pollen generates downward resistive pulses. Thus, it can be used to differentiate between pollen particles from other slightly charged or non-charged particles. FIG. 25 shows a scatter plot of the relative resistance $\delta R_c/R_c$ for the polymethacrylate particles and the pollen particles during a period of one second. The plot shows that there are four distinct regions of resistive pulses of the tested particles. The average resistive-pulse heights and the standard deviation are calculated and listed in Table 5.

TABLE 5

|  | Average relative resistive-pulse height ($\delta R_c/R_c$)(%) | Standard deviation (%) |
|---|---|---|
| 20 μm polymethacrylate | 0.23 | 0.104 |
| 40 μm polymethacrylate | 1.44 | 0.392 |
| Juniper pollen | −2.83 | 0.716 |
| Cottonwood pollen | −0.478 | 0.226 |

According to this example, polymethacrylate particles generate upward resistive pulses while pollen particles generate downward pulses. From FIG. 25, the 20 μm polymethacrylate particles and 40 μm polymethacrylate particles can be distinguished by size exclusion. In spite of the similar sizes of Juniper pollens and Cottonwood pollens (both are approximately 20 μm), the restive pulse heights generated by Juniper pollens are approximately six times higher than that of Cottonwood pollens. While not wishing to be bound to any one theory, the resistive-pulse difference might be attributed to the difference in the surface charge of pollen particles. Therefore, if the polymethacrylate particles and the pollen particles are mixed in DI water, one can distinguish and count them separately based on their resistive pulses. FIG. 25 also shows that the pulse heights of the Juniper tree pollen have more variations compared to the Cottonwood pollen. One explanation for this is that the variation is due to particle size variation and the egg shape of Juniper pollens.

FIG. 25 demonstrates that some embodiments of the present invention make it is possible to distinguish and count mixtures of various particles with similar sizes but different surface properties. In the following example an embodiment is demonstrated to be capable of distinguishing and counting mixtures of (1) 20 μm polymethacrylate particles and Juniper tree pollen, and (2) 20 μm polymethacrylate particles and Cottonwood pollen.

Twenty micrometer polymethacrylate particles, Cottonwood pollen and Juniper pollen solutions are prepared separately as set forth previously. Mixture 1 is prepared by combining 7 mL 20 μm polymethacrylate particle solution, and 3 mL Juniper pollen solution. Mixture 2 is prepared by combining 7 mL 20 μm polymethacrylate particle solution, and 3 mL Cottonwood pollen solution. The estimated polymethacrylate particle concentration is calculated to be $1.99 \times 10^5$ mL$^{-1}$ for both mixtures. The two particle mixtures are loaded to peripheral reservoirs 1 and 2, respectively. The microchannel diameters for channels 1 and 2 are 100 μm and 110 μm. Channels 3 and 4 are closed using polymer membranes without microchannels.

Figure 26A:
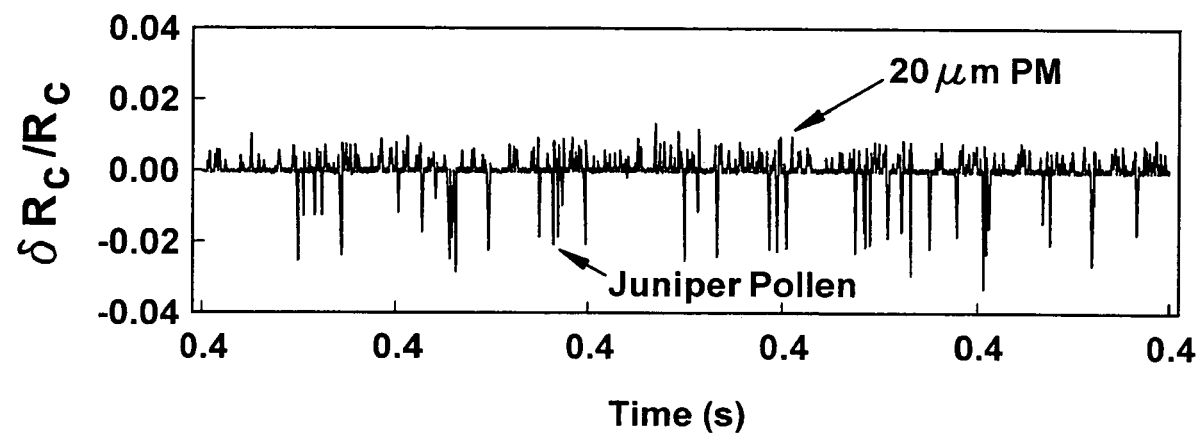
FIG. 26 is a plot of relative resistance as a function of time for (a) channel 1, and (b) channel 2.
Figure 26B:
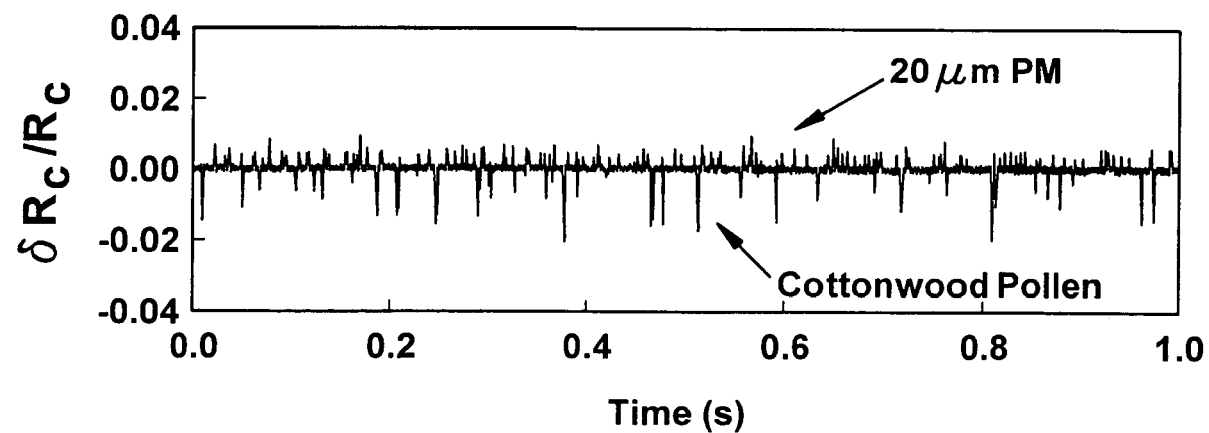

Typical traces of resistive pulses converted form the recorded voltage signal are shown in FIGS. 26(*a*) and (*b*). According to this data, 20 μm PM particles can be differentiated and counted based on the resistive pulses they generate.

The diameters and concentrations of polymethacrylate particles, calculated from experimental data in channels 1 and 2, are shown in Table 6.

Similar to the foregoing results of 20 μm polymethacrylate particles, the calculated particle diameters have larger variations than that which is specified by the manufacturer. The calculated concentrations of 20 μm polymethacrylate particles are $1.72 \times 10^5$ mL$^{-1}$ and $1.94 \times 10^5$ mL$^{-1}$, compared to the estimated actual concentration of $1.99 \times 10^5$ mL$^{-1}$.

TABLE 6

|  | Calculated particle size (μm) | Vendor's specification (μm) | Calc. particle conc. (mL$^{-1}$) | Est. particle conc. (mL$^{-1}$) |
| --- | --- | --- | --- | --- |
| μ-channel 1 (100 μm) Mixture 1 | 20.38 ± 2.51 | 20.00 ± 0.5 | $1.72 \times 10^5$ | $1.99 \times 10^5$ |
| μ-channel 2 (110 μm) Mixture 2 | 20.44 ± 2.27 | 20.00 ± 0.5 | $1 \times 10^5$ | $1.99 \times 10^5$ |

These results indicate that this multi-channel resistive-pulse sensor is capable of differentiating and counting multiple particle solutions through the four microchannels simultaneously. In contrast to a typical Coulter counter that can only analyze one particle solution, the sensor throughput is improved approximately 300%. The throughput can be further improved by fabricating more sensing channels in the device. The noise seen in the measured voltages averaged ±0.05 mV, so the device is capable of detecting particles that produce pulses larger than this noise level.

This suggests that the device is capable of detecting particles with diameters larger than approximately 8.9 μm, or 7.4% of the microchannel diameter. Sensitivity can be improved by improving shielding, and by the introduction of more sophisticated electronics to reduce the noise level. The multi-channel sensor reported herein combines size/surface charge exclusion separation and high throughput electronic detection in a simple device. The electrical properties or surface characteristics of biological particles are of great interest in recent years for novel rapid assays of these particles. These pollen results indicate that the multi-channel resistive-pulse device can be used to differentiate various pollen particles in terms of their surface characteristics and/or electrical properties. Although only four types of particles are tested, the resistive pulses due to the passage of various other biological particles are expected to exhibit distinct signals because of difference in electrical properties and/or surface characteristics of biological particles. Thus, some embodiments of the present invention provide a label-free means for detecting and counting biological particles. For instance, in addition to the size/surface charge exclusion, the measurement of the shape of the resistive pulses provides more detailed information of particles, including mobility, surface characteristics, electrical properties, and the like. In one embodiment, this could be done by reducing the particle travel velocity in the microchannel. Travel velocity can be controlled by forcing the particles to pass through microchannels using electrophoresis or a small pressure gradient, and by using a high sampling frequency.

Because of the simple structure of the multi-channel resistive-pulse device, throughput can be improved further by integrating more micro sensing channels. Further, some embodiments can comprise lab-on-a-chip devices having, for instance micromachined fluid channels, micro/nano-scale sensing channels and detection electronics. Additionally, use of multiple sensing channels enables multiplexing applications. This allows high throughput signal measurements with a high signal-to-noise ratio without compromising sensitivity. Therefore, the multi-channel resistive-pulse sensor embodiment can include a portable, high throughput micromachined device for micro and nano-scale bioparticle analysis.

Uncertainty analysis using the methods of Kline, Moffat and Coleman and Steele is carried out. There are three sources of uncertainty in the estimation of the particle size. The first source is due to uncertainty in the measurement of microchannel diameter and length. Due to the fabrication variation of the microchannel, these uncertainties are ±10% for diameter, and ±20% for channel length. These uncertainties contribute a ±10.5% uncertainty in particle size evaluation. Note that this source of uncertainty would systematically alter the estimated particle diameters.

The second source of uncertainty is due to the fluctuations in the output voltage, which are about ±0.05 mV at base voltage levels of 0.2 V. These fluctuations are due to measurement electronics and appear to have no systematic trend. According to Equation 5, this uncertainty contributes to an uncertainty of ±4.0% and ±0.7% in particle diameter estimation respectively for 20 μm particles and 40 μm particles.

The third source of uncertainty is due to the off-axis position when one particle passes through the microchannel. This results in a maximum uncertainty of about ±10% in the resistive pulse, which corresponds to an uncertainty of ±3.2% in particle size. Combining the three uncertainty sources, the uncertainties of particle size estimation are ±11.7% and 11% for 20 μm particles and 40 μm particles, respectively. The foregoing results show that the measurement error of the sensor is approximately within this uncertainty error range.

Figure 27:
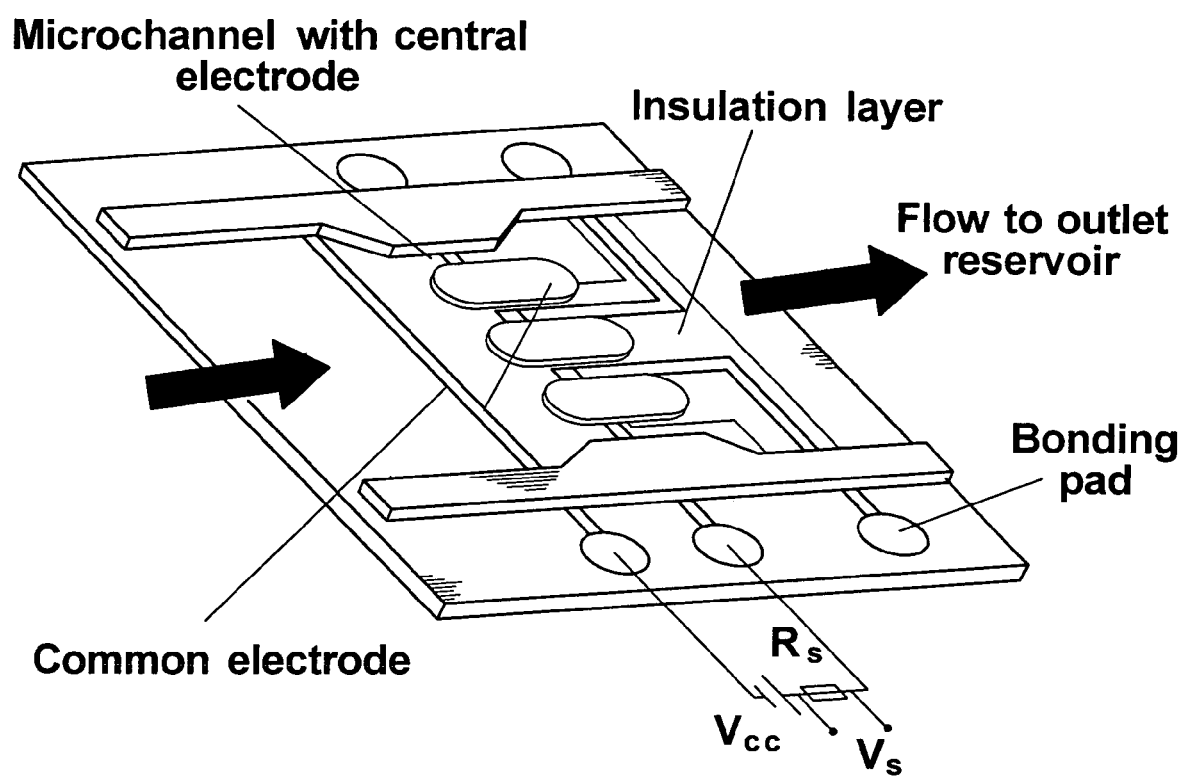
FIG. 27 is a schematic drawing of a micromachined multichannel resistive pulse sensor embodiment.

III. Microfluidic High-Throughput Resistive Pulse Sensor Embodiments:

The design concept of one embodiment is illustrated in FIG. 27. This embodiment comprises a multichannel resistive pulse sensor. The sensor comprises a single inlet reservoir and a single outlet reservoir, connected by four microchannels of dimensions 50 μm×100 μm×300 μm. The device has a common electrode placed in the inlet reservoir at the entrance of the microchannels and four central electrodes fabricated at the centers of the four microchannels. Each central electrode is exposed to the electrolyte only at the center of the channel for measurement purposes. The measurement setup for one channel is illustrated in FIG. 27, and comprises a constant DC power supply $V_{cc}$ connected to the common electrode at one end and to a sampling resistor at the other end. Electrolyte containing particles is forced to move from the inlet reservoir to the outlet reservoir through a plurality of sensing channels. When a particle passes through a channel, it causes a change in the resistance of the electrolyte-filled channel, thereby resulting in a voltage pulse across the sampling resistor of that channel. The voltage pulses across each sampling resistor can be recorded and analyzed separately. In contrast to a single channel Coulter counter, the sensor can detect particles through its four sensing channels simultaneously. Thus, the design enables high throughput.

Figure 28:
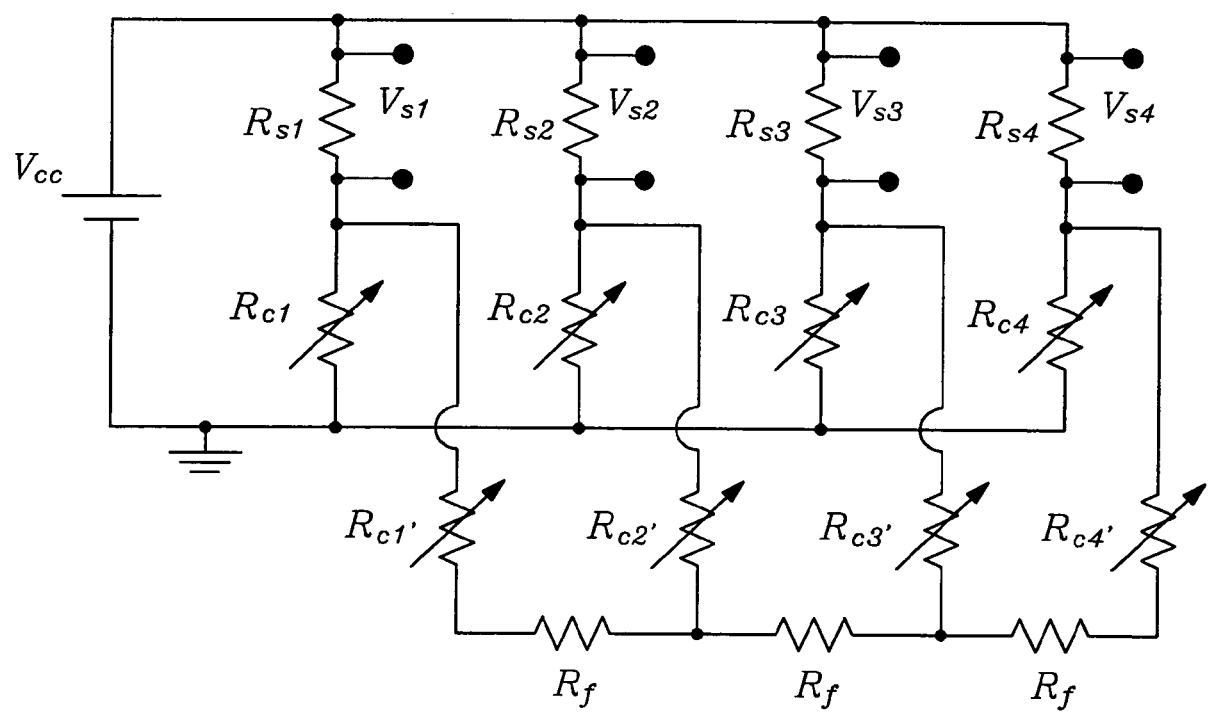
FIG. 28 is an electrical schematic showing a simplified model of a multichannel resistive pulse sensor embodiment.

A simplified electrical circuit equivalent of the measurement setup is shown in FIG. 28. The measurement electrode in the center of a sensing channel divides that channel into two equivalent resistances $R_{ci}$ and $R_{ci'}$ (i=1,2,3,4). The first half of each microchannel ($R_{ci}$) serves as a sensing channel, while the second half of each microchannel serves as an isolation resistor to reduce or eliminate crosstalk among channels. When a particle passes through channel i, it affects first the equivalent resistance of the first half of the channel $R_{ci}$, and then the equivalent resistance of the second half $R_{ci'}$. The change is dependent on both the particle's size and amount of surface charge. $R_{si}$ is the sampling resistor of the microchannel, across which the recorded voltage $V_{si}$ is measured. $R_{si}$ is the resistance formed by the electrolyte between two adjacent microchannels. This resistance is usually small compared to microchannel resistance and is therefore neglected.

One challenge for using multiple sensing channels is the electronic coupling or crosstalk among channels because the electrolyte electrically connects all channels. When one particle passes through a microchannel, it generates a resistance change in this channel. Because all channels are electrically connected, a resistance change in one channel can cause a current change in other channels, and in turn induce a voltage change across the sampling resistors of other microchannels. This voltage change can be translated into a change in resistance signals of other channels that do not correspond to passing particles, thereby resulting in false detections. The placement of measurement electrodes in the center of microchannels creates an isolation resistor $R_{ci'}$ between each pair of microchannels (see FIG. 28) and reduces the crosstalk.

Figure 29:
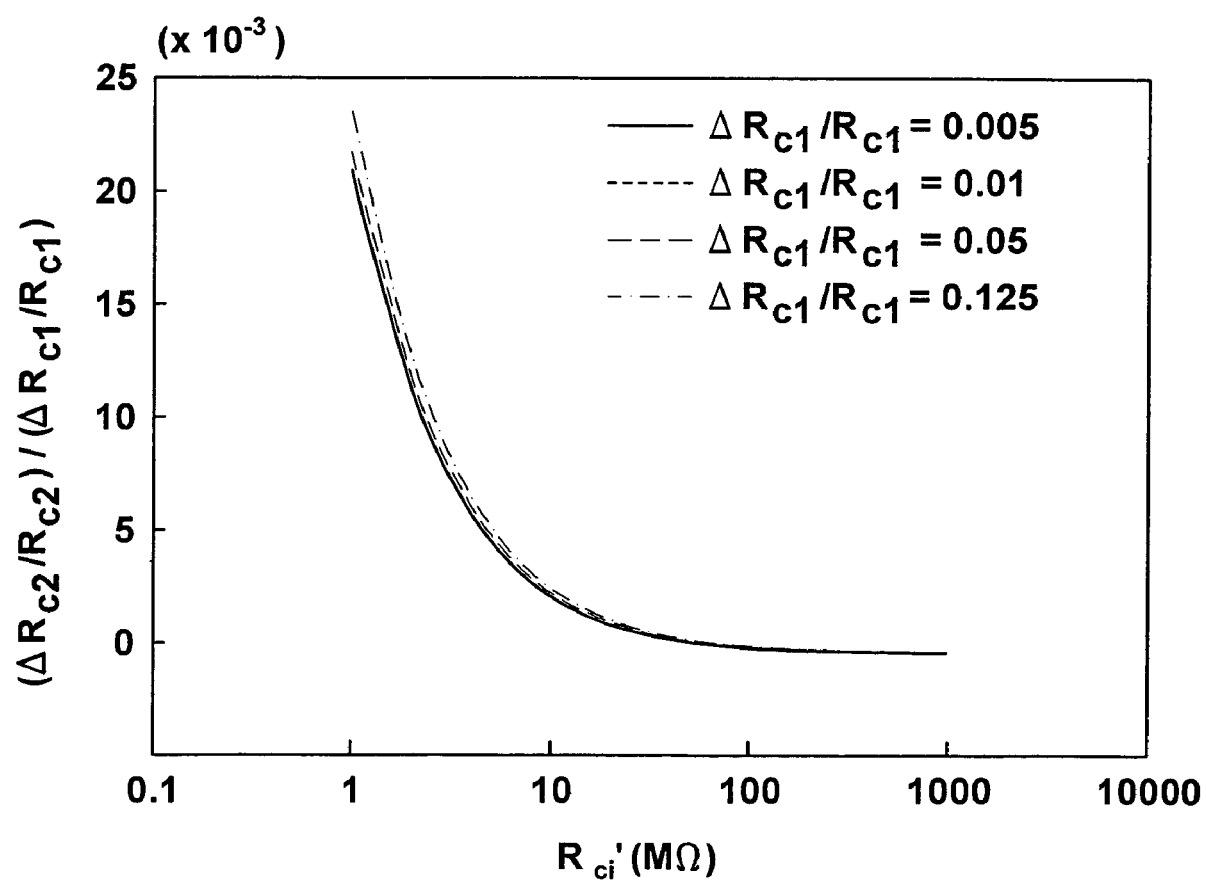
FIG. 29 is a typical crosstalk analysis between adjacent microchannel.

FIG. 29 shows the result of a typical crosstalk analysis of our device using PSpice® (PSpice® can be obtained from Cadence, Inc. of San Jose, Calif.) assuming $R_{ci}=R_{ci'}$. When the isolation resistance $R_{ci'}$ is 10MΩ, the relative crosstalk $(\Delta R_2/R_2)/(\Delta R_1/R_1)$ in the adjacent channel (where the crosstalk is maximal) is approximately 0.2% and is considered negligible. As the isolation resistance increases, the crosstalk is further reduced. When $R_{ci'}=100$ MΩ, the cross talk is approximately zero.

The resistance of a microchannel can be estimated by $R=\rho L/A$, where $\rho$ is the resistivity of the electrolyte, L is the length of the microchannel, and A is the cross section of the microchannel. In this work, we use deionized (DI) water, with a resistivity of about $8.33\times10^3$ Ω-m, to carry the microparticles. For the microchannel we used, the estimated resistance of the DI water filled-microchannel ($R_{ci'}$) is in the order of 100 MΩ. Thus, the crosstalk is negligible. When the channel size is scaled down to the submicron and nanometer level, according to the scaling law, $R_{ci'}$ will be increased significantly, and thus much less crosstalk is expected. Therefore, some embodiments having nanoscale channels can operate without crosstalk even when using a more concentrated electrolyte having a lower resistivity. This is particularly useful because, concentrated electrolytes are often necessary for carrying certain bio-particles.

The microchannels and reservoirs are fabricated on polydimethylsiloxane (PDMS) using soft lithography, and are bonded to a glass substrate with sputter gold electrodes. Device layout (microfluidic channels and electrodes) can be printed onto transparency films using a high-resolution laser printer. The transparency films can then be used as masks in contact photolithography to generate masters with a negative UV photoresist (MicroChem Corporation XP SU-8 2010, Newton, Mass.) on a glass slide for the channels.

According to one example, a curing agent and PDMS prepolymer (SYLGARD 184 Silicone Elastomer Kit, Dow Corning, Midland, Mich.) are mixed in a 1:10 weight ratio. The prepolymer mixture is degassed in a desiccator with a vacuum pump for one hour to remove any air bubbles in the mixture. Then, the prepolymer mixture is poured onto the master. The master/PDMS stack is cured for three hours at 80° C. on a hot plate. After curing, the thin PDMS replicas are cut and peeled off of the masters. Next, contact photolithography with a positive AZ 4620 photoresist (AZ Electronic Materials, Somerville, N.J.) is presented on another glass slide to create the electrode patterns. Cr/Au (50 Å/3000 Å) sheet films are evaporated on the glass slide. A subsequent liftoff process completes fabrication of the electrodes. The PDMS layer with developed channels and electrodes-embedded glass slide are then treated with RF oxygen plasma (Plasma Etcher PE 2000, South Bay Technology Inc., San Clemente, Calif.) for 25 seconds (50 W, 200 mTorr). This temporarily activates the exposed part of the PDMS and provides very good adhesion. The PDMS replica and glass side are then immediately brought into contact, aligned, and bonded together.

A single measurement channel comprises the half channel resistance $R_{ci}$ in series with the sampling resistor $R_s$ and the supply voltage (see FIG. 27). When a particle passes through the microchannel it causes a change in the half channel resistance, and a corresponding change in the voltage across the sampling resistor. The relative change in resistance of the microchannel in terms of the measured voltage is given by Equation (1), where $V_s'$ is the measured voltage when a particle is present in the microchannel and $V_s$ is the measured voltage in the absence of a particle in the microchannel.

For a micro-channel with length L and diameter D (see FIG. 28(b)), the change in resistance as a particle passes through it is given by Equation (2), where d is the diameter of the particle, and D and L are the diameter and length of the micro-channel, respectively. The equation holds true when $(d/D)^3<0.1$, as is the case in this embodiment. Thus, the particle diameter can be calculated from the relative change in resistance according to Equation (3).

Figure 30A:
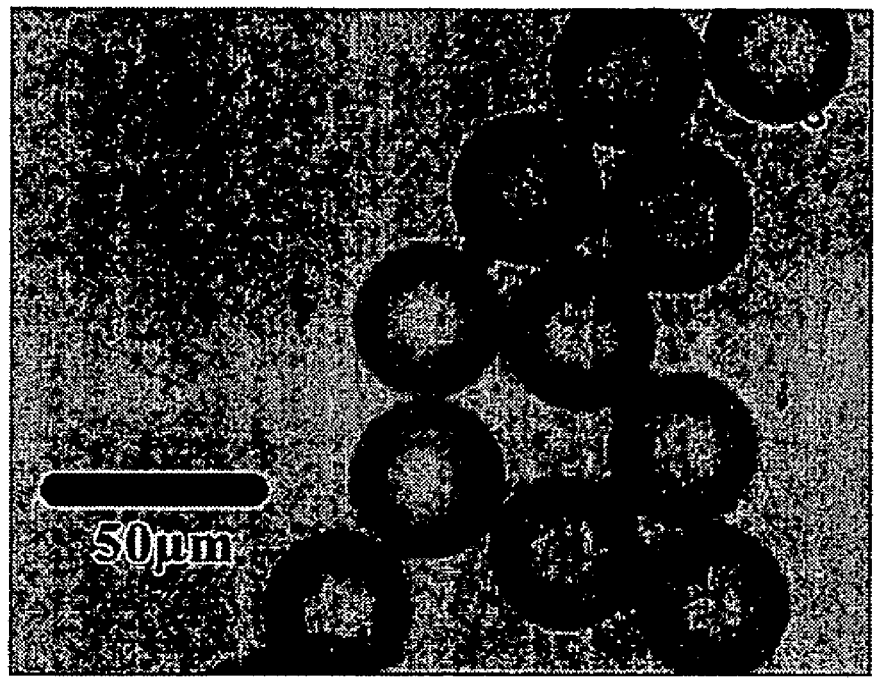
FIG. 30 is a pair of photomicrographs showing (a) 40 μm PM particles, and (b) Juniper Scopulorum pollen.
Figure 30B:
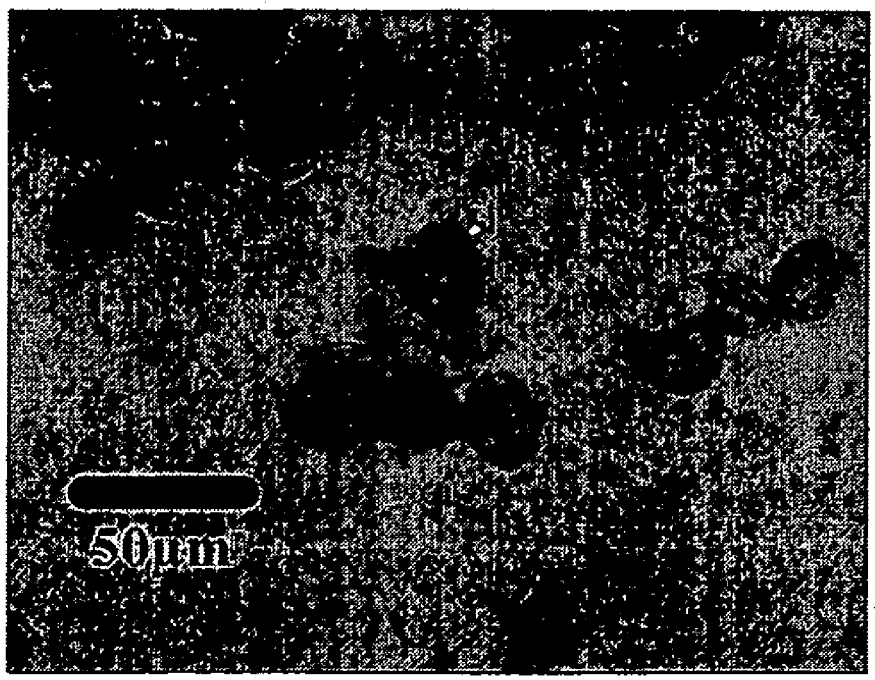

An illustration of this embodiment follows. Polymethacrylate particles with diameters of 40 μm (40 μm±0.8 μm) (Sigma Aldrich Inc.), and Rocky mountain Juniper (Juniper Scopulorum) tree pollens (Sigma Aldrich Inc.) are chosen for the following example. These particles are chosen because they are commercially available and because polymethacrylate particles have well characterized properties. The diameters of pollen particles are determined using high resolution optical microscopy. The Juniper tree pollen is egg-shaped and the diameter ranges from 17 μm to 23 μm. FIGS. 30(a), and 30(b) show photomicrographs of 40 μm polymethacrylate particles and Juniper tree pollen, respectively.

The particle solution is forced to flow through microchannels of the present invention by application of a pressure difference with a syringe. An applied voltage of $V_{cc}=6V$ is applied across the microchannels. Due to the polarization effect of gold electrodes, such a high source voltage is necessary to ensure that there is sufficient current/electric field within the electrolyte to record a noticeable voltage change across the sampling resistors. Voltage measurements are made across a sampling resistor $R_s=100$ kΩ. The voltage trace is recorded for four channels using a National Instruments NI-6220 data acquisition board, with a sampling frequency of 50 kHz.

The application of a 6V DC voltage on the electrodes in electrolyte can, in some cases, cause electrolysis of water and generate gas bubbles. The gas bubbles can result in false peaks when they pass through the microchannel. No such bubbles are observed in this example.

Figure 31:
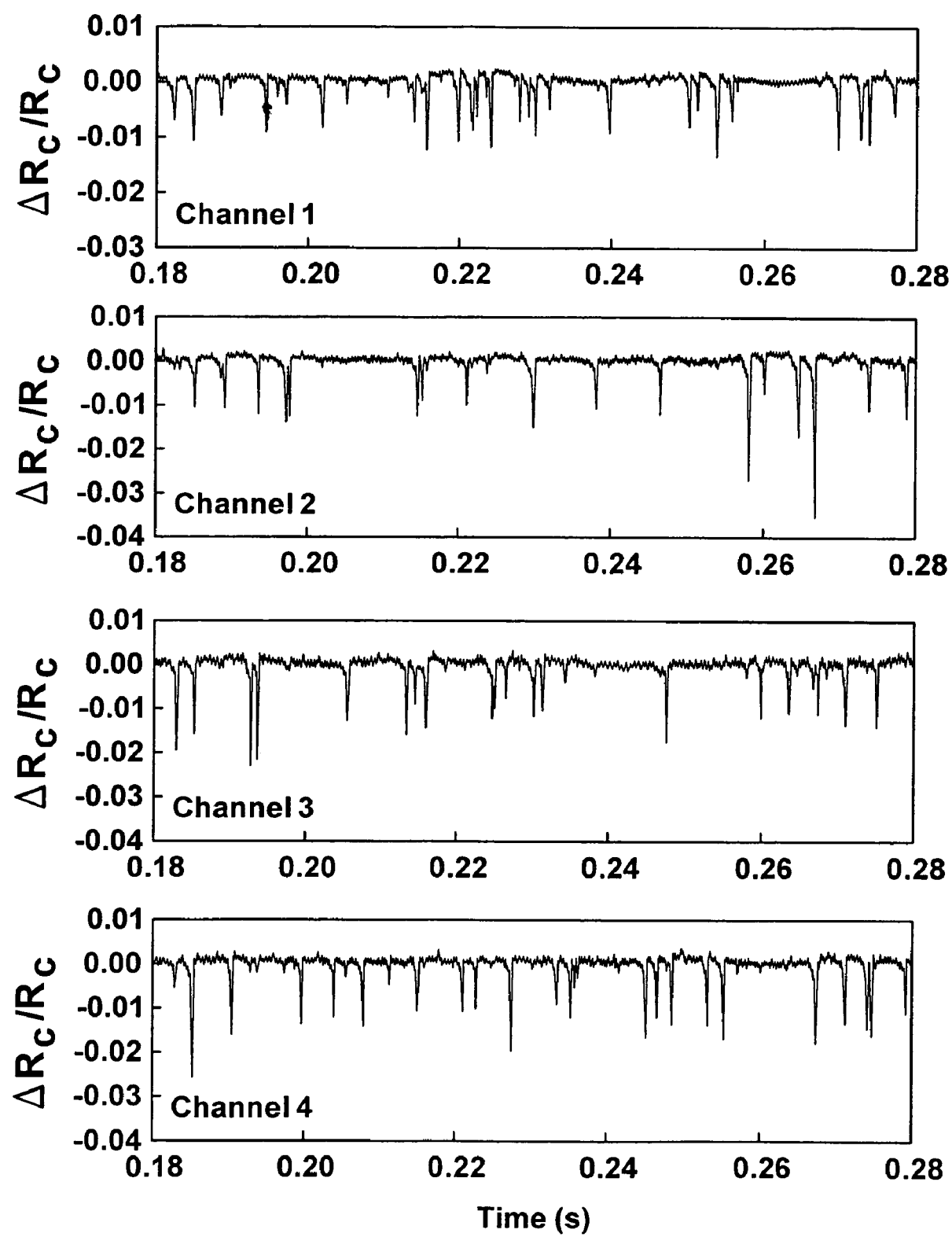
FIG. 31 is a set of plots showing typical relative resistance traces from four channels.
Figure 32:
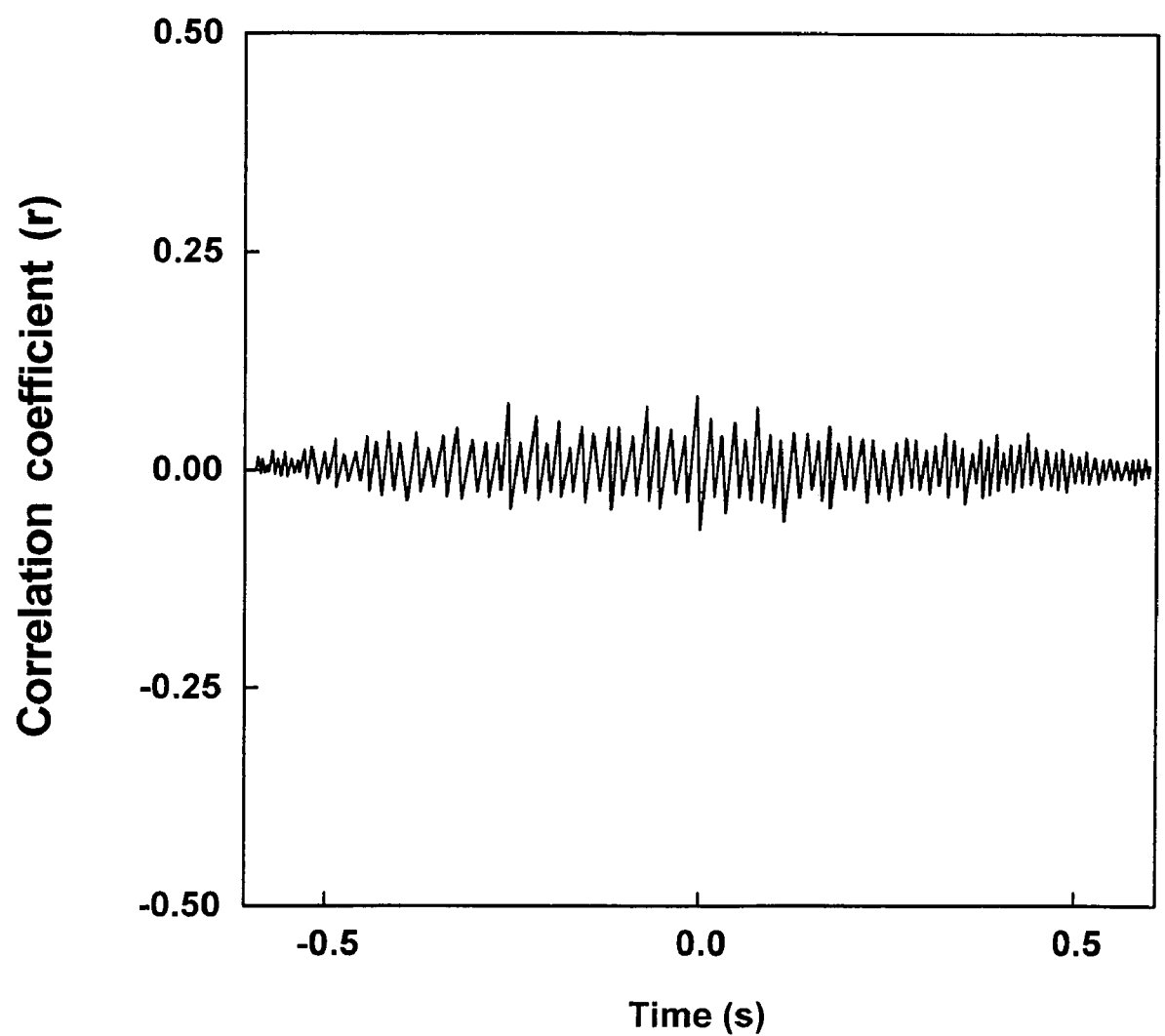
FIG. 32 is a typical cross correlation analysis for adjacent channels.

The Juniper pollen particle solution is prepared by diluting 10 mg of Juniper tree pollen in 10 mL of water. FIG. 31 shows the relative resistance change of the four channels as a function of time. Resistance is calculated by converting it from voltage traces measured across the four sampling resistors using Equation (1). Each resistive pulse represents one pollen particle passing through a microchannel. The resistive traces show pulses appearing in random sequence. A cross correlation analysis is performed between the signals from two sensing channels at a time. The results are shown in FIG. 32. These results show that the cross correlation coefficients |r| are all less than 0.1, indicating there is negligible correlation among the pulses of different channels. Thus, the four sensing channels are able to simultaneously detect and count particles with negligible crosstalk among channels.

It is obvious from FIG. 31 that the resistive pulses caused by Juniper pollens are all downward, that is, when a pollen particle passes through the microchannel, the microchannel resistance decreases. This is possibly because of the high surface charge of pollen particles. This phenomenon can be explained in terms of the surface charge of particles, and can be used to distinguish between particles with different surface charges. Notably, the pulses of the Juniper pollen vary in height. Although not wishing to be bound to any one theory, the variation might be attributed to the particle size variation and the egg-shape of Juniper pollen.

Figure 33:
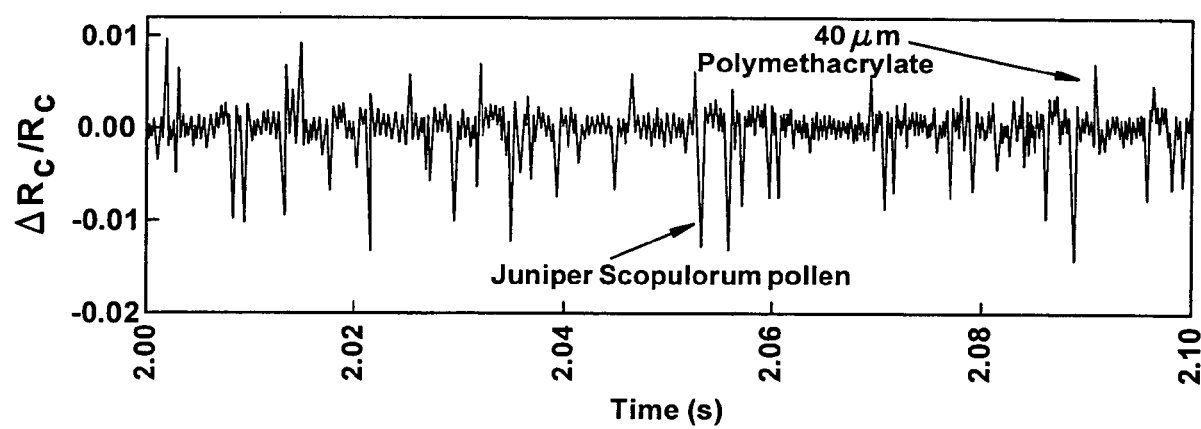
FIG. 33 is a typical relative resistance for a mixture of Juniper pollen and 40 μm PM particles in a one-channel embodiment.
Figure 34A:
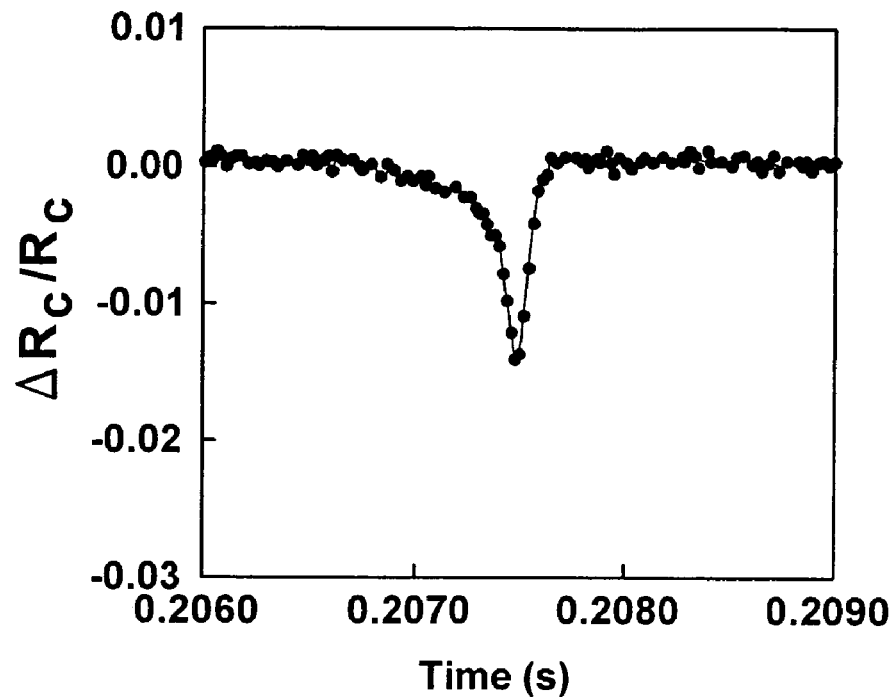
FIG. 34 is a pair of magnified resistive pulses due to (a) Juniper pollen, and (b) 40 μm PM particles.
Figure 34B:
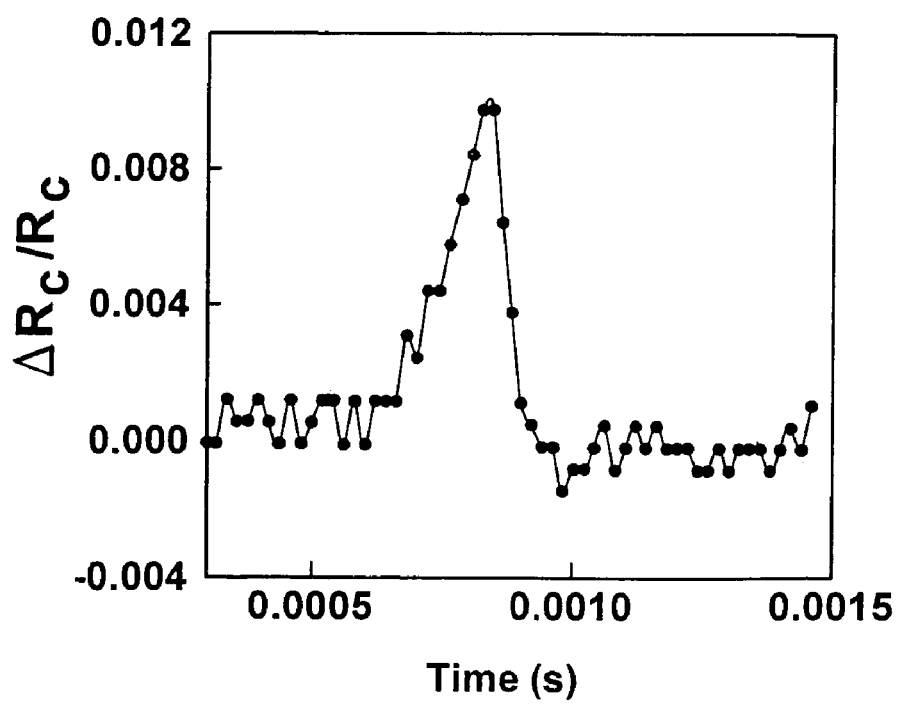
Figure 35:
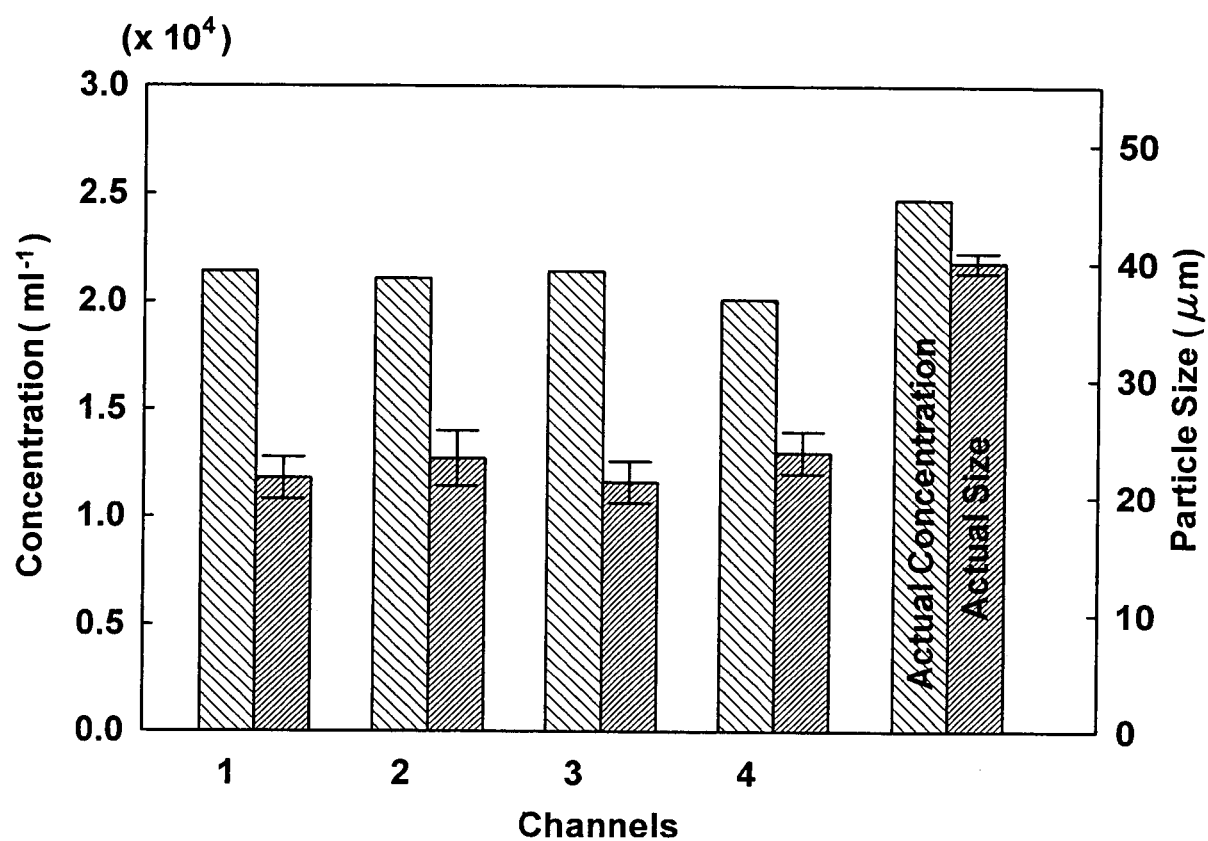
FIG. 35 is a graphical summary of the measured diameter and concentration of 40 μm PM particles in a mixture.

Polymethacrylate particle solution (10% solid) 0.1 mL of 40 μm, and 10 mg Juniper pollen are mixed in 10 mL DI water and are tested in a multichannel embodiment. The resulting concentration of 40 μm polymethacrylate particles is $2.49 \times 10^4$ $mL^{-1}$. Voltage traces across the sampling resistors are recorded. A typical resistive pulse trace in one channel (channel 3) is shown in FIG. 33. The resistive trace is converted from the voltage trace signal. Magnified resistive pulses generated by Juniper pollen and 40 μm polymethacrylate particle are shown in FIG. 34. According to these results, pollen generates downward resistive pulses, while polymethacrylate particles generated upward resistive pulses. Thus, we are able to differentiate and count the two particle species. The concentration of the 40 μm polymethacrylate particles in the four channels is calculated from counting the number of upward peaks during the period of one second. The concentrations are calculated to be $2.15 \times 10^4$ $mL^{-1}$, $2.11 \times 10^4$ $mL^{-1}$, $2.14 \times 10^4$ $mL^{-1}$, and $2.01 \times 10^4$ $mL^{-1}$ for channels 1, 2, 3 and 4, respectively. These results are shown in FIG. 35. The measured particle concentration in each channel is lower than the estimated particle concentration, which is $2.49 \times 10^4$ $mL^{-1}$. This may be due to some PM particles depositing onto the substrate during the experiment.

The particle diameters are calculated from resistive pulse data shown in FIG. 33 using Equations (2) and (3). Using the nominal sensing microchannel dimension of 50 μm×100 μm×150 μm, the analysis shows the estimated particle diameter is 20.1±1.8 μm, 20.4±1.5 μm, 22.0±2.1 μm, and 22.4±1.8 μm for channels 1, 2, 3 and 4, respectively (see FIG. 35). The large difference between the calculated and the actual particle diameter (40 μm±0.8 μm) is mainly because of the polarization effect that takes place on the gold electrodes. In electrolyte solution and DI water, electrode polarization causes the DC voltage applied on electrodes be dropped across the double layers of the two electrodes. Thus, the voltage drop across the bulk solution is less than the actual applied voltage, resulting in underestimated particle dimensions when Equation (3) is used. The electrode polarization can be reduced by using Ag/AgCl electrodes with large surface areas.

The foregoing examples are considered only illustrative of the principles of the invention rather than an exclusive list of embodiments. Further, since numerous modifications and changes will readily occur to those of ordinary skill in the art, the invention is not intended to be limited to the exact construction and operation shown and described, and accordingly, all suitable modifications and equivalents are within the scope of the present invention.

What is claimed is:

1. A multichannel particle counting device comprising:
    a means for dividing a first reservoir and a second reservoir;
    the means further comprising at least one orifice disposed between the first reservoir and the second reservoir through which the first and second reservoirs maintain fluid communication;
    the at least one orifice further including a control electrode, wherein each control electrode is substantially electrically isolated from any other control electrodes;
    each control electrode connected to a single circuit that superpositions all control electrode signals;
    the first reservoir including a first electrode, which electrode is in electrical communication with a power supply;
    the second reservoir including a second electrode, which electrode is in electrical communication with a measuring circuit;
    the reservoirs containing an electrolyte solution; and
    a means for creating a net fluid flow of electrolyte from one reservoir to the other reservoir.

2. The multichannel particle counting device of claim 1, wherein the means for dividing the first and second reservoirs comprises a membrane.

3. The device of claim 2, wherein the membrane comprises one or more materials selected from organic polymers, silicon, p-type silicon, and GaAs.

4. The device of claim 3, wherein organic polymers include polymethyl methacrylates, polycarbonates, polyimides, polyphenols, and chlorinated polyolefins.

5. The device of claim 2, wherein the control electrode controls the flow of particles through an associated orifice.

6. The device of claim 2, wherein the control electrode comprises a material selected from one or more of AgIAgCl, platinum, and graphite.

7. The device of claim 2, wherein the first and second electrodes are selected from AgIAgCl, platinum, and graphite.

8. The device of claim 2, further comprising a means for collecting electrical current pulse data from the plurality of orifices.

9. The device of claim 8, further comprising a means for processing the data collected.

10. A method for rapidly counting particles comprising the steps of:
    charging one reservoir of the device of claim 1 with at least one particle to be measured;
    applying a voltage across the first and second electrodes;
    allowing the particles to migrate from one reservoir to the other through the plurality of orifices;
    detecting the signals generated by particles passing through the plurality of orifices using a single detection circuit;
    deconvoluting the signals detected;
    correlating the signals to a number of particles for each individual channel; and
    counting the deconvoluted signals.

11. The method of claim 10, wherein the particle to be measured is selected from one or more of pollen, dust, airborne contaminants, microbes, viruses, and biological warfare agents.

12. The method of claim 11 wherein biological warfare agents comprise one or more of Anthrax, Botulinum Toxin, Brucellosis, Cholera, Clostridium Perfringens Toxin, Crimean-Congo Hemorrhagic Fever, Ebola Hemorrhagic Fever, Melioidosis, Plague, Q Fever, Ricin, Rift Valley Fever, Saxitoxin, Smallpox, Staphylococcal Enterotoxin B, Trichthecene Mycotoxin, Tularemia, and Venezuelan Equine Encephalitis.

13. The method of claim 10, wherein the applied voltage is between 1 and 4 volts.

14. The method of claim 10, wherein the signals comprise current and/or voltage pulses.

15. The method of claim 10, wherein the step of deconvoluting further comprises applying the Hadamard transformation or Fast Fourier Transformation to the signal data.

16. The device of claim 2, wherein the plurality of orifices comprises between 2 and 106 orifices.

17. The multichannel particle counting device of claim 1, wherein the means for dividing the first and second reservoirs further comprises microfluidic channels.

18. The multichannel particle counting device of claim 17, wherein the microfluidic channel is formed according to a method selected from one or more of lithography and micromachining.

19. The multichannel particle counting device of claim 1, wherein the control electrode controls the flow of particles through an associated orifice.

20. The multichannel particle counting device of claim 1, wherein the first and second electrodes are selected from AgIAgCl, platinum, and graphite.

* * * * *